United States Patent
Aissaoui et al.

(10) Patent No.: US 7,834,028 B2
(45) Date of Patent: Nov. 16, 2010

(54) PYRAZOLO-TETRAHYDRO PYRIDINE DERIVATIVES AS OREXIN RECEPTOR ANTAGONISTS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 12/298,369

(22) PCT Filed: Apr. 25, 2007

(86) PCT No.: PCT/IB2007/051522

§ 371 (c)(1),
(2), (4) Date: Oct. 24, 2008

(87) PCT Pub. No.: WO2007/122591

PCT Pub. Date: Nov. 1, 2007

(65) Prior Publication Data

US 2009/0099228 A1    Apr. 16, 2009

(30) Foreign Application Priority Data

Apr. 26, 2006    (WO) ............... PCT/IB2006/051300

(51) Int. Cl.
*A61K 31/44* (2006.01)
*C07D 471/02* (2006.01)

(52) U.S. Cl. ..................... 514/303; 546/119
(58) Field of Classification Search ............... 546/119; 514/303
See application file for complete search history.

(56) References Cited

U.S. PATENT DOCUMENTS

| 6,703,392 | B2 | 3/2004 | Aissaoui et al. |
| 7,192,950 | B2 | 3/2007 | Aissaoui et al. |
| 2004/0044031 | A1 | 3/2004 | Yamada et al. |
| 2006/0178515 | A1 | 8/2006 | Aissaoui et al. |
| 2007/0191424 | A1 | 8/2007 | Aissaoui et al. |
| 2009/0082394 | A1 | 3/2009 | Jenck |

FOREIGN PATENT DOCUMENTS

| WO | WO01/68609 | 9/2001 |
| WO | W02/051838 | 7/2002 |
| WO | WO03/091219 | 11/2003 |
| WO | WO2004/085403 | 10/2004 |
| WO | WO2005/118548 | 12/2005 |
| WO | WO2006/024779 | 3/2006 |

OTHER PUBLICATIONS

Cai et. al., "Antagonists of the orexin receptors", Expert Opinion Ther. Patents (2006) 16(5); pp. 631-646.*

* cited by examiner

*Primary Examiner*—Janet L Andres
*Assistant Examiner*—Binta M Robinson
(74) *Attorney, Agent, or Firm*—Hoxie & Associates LLC

(57) ABSTRACT

The invention relates to novel pyrazolo-tetrahydropyridines compounds and their use as orexin receptor antagonists.

19 Claims, No Drawings

PYRAZOLO-TETRAHYDRO PYRIDINE DERIVATIVES AS OREXIN RECEPTOR ANTAGONISTS

CROSS REFERENCE TO RELATED APPLICATIONS

This application is a United States Application under 35 U.S.C. 371 claiming benefit of PCT Application No. PCT/IB2007/051522, filed on Apr. 25, 2007, which claims the benefit of PCT Application No. PCT/IB20061051300, filed on Apr. 26, 2006, the contents of each of which are incorporated herein by reference in their entirety.

The present invention relates to novel compounds of formula (I) and/or (Ia) and their use as pharmaceuticals. The invention also concerns related aspects including processes for the preparation of the compounds, pharmaceutical compositions containing one or more compounds of formula (I) and/or (Ia), and especially their use as orexin receptor antagonists.

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions.

The present invention provides substituted 1,2,3,4-tetrahydro-pyrrolo[1,2-a]pyrazine and 5,6,7,8-tetrahydro-imidazo[1,5-a]pyrazine derivatives, which are non-peptide antagonists of human orexin receptors, in particular $OX_2$ receptors. These compounds are in particular of potential use in the treatment of e.g. eating disorders, drinking disorders, sleep disorders, or cognitive dysfunctions in psychiatric and neurologic disorders.

Up to now, some low molecular weight compounds are known having a potential to antagonise either specifically $OX_1$ or $OX_2$, or both receptors at the same time. In WO01/85693, Banyu Pharmaceuticals claimed N-acyltetrahydroisoquinoline derivatives. Other orexin receptor antagonists such as novel benzazepine derivatives (WO02/051838), and 1,2,3,4-tetrahydroisoquinoline derivatives (WO01/68609, WO2004/085403) are disclosed by Actelion Pharmaceuticals Ltd. Furthermore, the use of solution-phase chemistry for the lead optimization of 1,2,3,4-tetrahydroisoquinoline derivatives as potential orexin receptor antagonists has been reported (Chimia, 2003, 57, 5, 270-275).

A first aspect of the invention consists of a compound of the general formula I

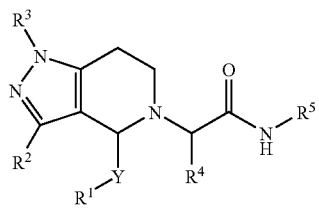

General Formula I wherein

Y represents —$CH_2$—$CH_2$—;

$R^1$ represents 1,3-benzodioxole or a phenyl group, wherein the phenyl group can be mono-, di-, or tri-substituted, wherein the substituents are independently selected from the group consisting of ($C_{1-4}$)alkyl, halogen and trifluoromethyl;

$R^2$ represents ($C_{1-4}$)alkyl;

$R^3$ represents ($C_{1-4}$)alkyl;

$R^4$ represents a phenyl group, wherein the phenyl group is unsubstituted or independently mono-, di-, or trisubstituted wherein the substituents are independently selected from the group consisting of ($C_{1-4}$)alkyl and halogen;

$R^5$ represents ($C_{1-4}$)alkyl.

The compounds of the general formula I and/or Ia (see below) contain one or more asymmetric carbon atoms and may be prepared in form of optically pure enantiomers, mixtures of enantiomers such as racemates, diastereomers, mixtures of diastereomers, diastereomeric racemates, mixtures of diastereomeric racemates, or meso-forms.

The compounds of the general formula I and/or Ia (see below) also encompass the pharmaceutically acceptable salts thereof.

In the present description the term "halogen" means fluorine, chlorine, bromine or iodine and preferably fluorine or chlorine. In a further preferred embodiment of the invention the term "halogen" means fluorine.

The term "($C_{1-4}$)alkyl", alone or in combination, means a straight-chain or branched-chain alkyl group with 1 to 4 carbon atoms. Examples of ($C_{1-4}$)alkyl groups are methyl, ethyl, propyl, isopropyl, n-butyl, isobutyl, sec.-butyl or tert.-butyl; in analogy the term "($C_{2-4}$)alkyl" means a straight-chain or branched-chain alkyl group with 2 to 4 carbon atoms; the term "($C_{1-2}$)alkyl" means a methyl or ethyl group. Preferred are methyl and ethyl.

For the substituent $R^2$ or $R^5$ the term "($C_{1-4}$)alkyl" preferably means methyl.

For the substituent $R^3$, the term "($C_{1-4}$)alkyl" preferably means methyl, ethyl or butyl.

The term "aryl", alone or in combination, means a phenyl or a naphthyl group. Preferred is a phenyl group. The aryl group may also be independently mono-, di-, or trisubstituted wherein the substituents are independently selected from the group consisting of ($C_{1-4}$)alkyl, ($C_{1-4}$)alkoxy, halogen, cyano, trifluoromethyl, trifluoromethoxy, $NR^8R^9$, $N(R^8)C(O)R^9$, and $C(O)NR^8R^9$. Preferred substituents are independently selected from the group consisting of ($C_{1-4}$)alkyl, halogen and trifluoromethyl. Examples are trifluoromethyl-phenyl (eg 4-trifluoromethyl-phenyl), chloro-phenyl (2-chloro-phenyl, 3-chloro-phenyl and 4-chloro-phenyl), methyl-phenyl (eg 2-methyl-phenyl, 3-methyl-phenyl, 4-methyl-phenyl), dimethyl-phenyl (eg 2,3-dimethyl-phenyl, 2,4-dimethyl-phenyl), dimethoxy-phenyl (eg 2,5-dimethoxy-phenyl, 2,4-dimethoxy-phenyl), fluoro-methoxy-phenyl (eg 3-fluoro-4-methoxy-phenyl), dichloro-phenyl (eg 2,4-dichloro-phenyl), difluoro-phenyl (eg 3,4-difluoro-phenyl).

$R^1$ is preferably substituted by methyl, ethyl, isopropyl, trifluoromethyl, fluorine, chlorine, or methoxy. More preferred $R^1$ is substituted by methyl, ethyl, trifluoromethyl, fluorine or chlorine. Said groups are preferred substituents for the aryl group.

For the substituent $R^4$ the term "aryl" preferably means phenyl.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of formula (I) and/or (Ia) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

Salt-forming groups are groups having basic or acidic properties. Compounds having at least one basic group, for example amino, a secondary amino group not forming a peptide bond or a pyridyl group, may form acid addition salts, for example with inorganic acids. When several basic groups are present mono- or poly-acid addition salts may be formed.

Compounds having acidic groups, such as a carboxyl group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts/zwitterions.

For the purposes of isolation or purification, as well as in the case of compounds that represent intermediates, it is as well possible to use pharmaceutically unacceptable salts, e.g. the picrates. However, only pharmaceutically acceptable, non-toxic salts may be used for therapeutic purposes, and are therefore preferred.

The present invention encompasses all these forms. Mixtures can be separated in a manner known per se, e.g. by column chromatography, thin layer chromatography (TLC), high performance liquid chromatography (HPLC), or crystallization.

The present invention encompasses also solvation complexes of compounds of general formula I and/or Ia. The solvation can be effected in the course of the manufacturing process or can take place separately, e.g. as a consequence of hygroscopic properties of an initially anhydrous compound of general formula I and/or Ia.

The compounds specifically mentioned above contain two centers of chirality. The more preferred stereoisomers exhibit the chirality as depicted below (see general formula Ia):

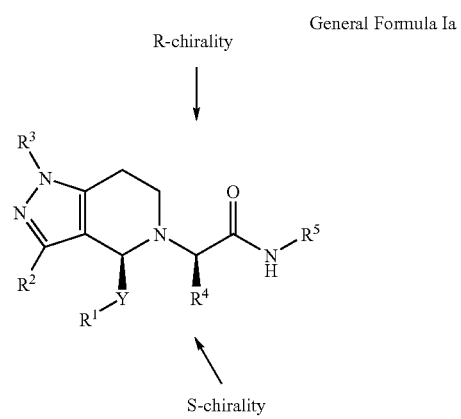

General Formula Ia

A further embodiment of the invention are compounds of formula I and/or Ia wherein Y represents —$CH_2$—$CH_2$—;

$R^1$ represents 1,3-benzodioxole or a phenyl group, wherein the phenyl group can be mono-, di-, or tri-substituted, wherein the substituents are independently selected from the group consisting of ($C_{1-4}$)alkyl, halogen and trifluoromethyl;

$R^2$ represents ($C_{1-4}$)alkyl;

$R^3$ represents ($C_{1-4}$)alkyl;

$R^4$ represents a phenyl group;

$R^5$ represents ($C_{1-4}$)alkyl.

A further embodiment of the invention are compounds of formula I and/or Ia wherein Y represents —$CH_2$—$CH_2$—;

$R^1$ represents 1,3-benzodioxole or a phenyl group, wherein the phenyl group can be mono-, di-, or tri-substituted, wherein the substituents are independently selected from the group consisting of methyl, ethyl, fluorine, chlorine and trifluoromethyl;

$R^2$ represents methyl;

$R^3$ represents ethyl;

$R^4$ represents a phenyl group;

$R^5$ represents methyl.

Especially preferred compounds are listed below:

2-{1-Ethyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide;

2-{1-Ethyl-4-[2-(4-ethyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide;

2-{4-[2-(2,3-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-3-methyl-4-[2-(2,3,5-trifluoro-phenyl)-ethyl]-1,4,6,7-tetrahydro-pyrazolo[4,3-c]pyridin-5-yl}-N-methyl-2-phenyl-acetamide;

2-[1-Ethyl-3-methyl-4-(2-p-tolyl-ethyl)-1,4,6,7-tetrahydro-pyrazolo[4,3-c]pyridin-5-yl]-N-methyl-2-phenyl-acetamide;

2-{1-Ethyl-4-[2-(4-fluoro-3-methyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-3-methyl-4-[2-(3-trifluoromethyl-phenyl)-ethyl]-1,4,6,7-tetrahydro-pyrazolo[4,3-c]pyridin-5-yl}-N-methyl-2-phenyl-acetamide;

2-[4-(2-Benzo[1,3]dioxol-5-yl-ethyl)-1-ethyl-3-methyl-1,4,6,7-tetrahydro-pyrazolo[4,3-c]pyridin-5-yl]-N-methyl-2-phenyl-acetamide;

2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(4-isopropyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(3-fluoro-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-4-methyl-phenyl)-ethyl]-3-methyl-1,4,6,7-tetrahydro-pyrazolo[4,3-c]pyridin-5-yl}-N-methyl-2-phenyl-acetamide;

2-{4-[2-(2,3-Difluoro-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(2-fluoro-3-methyl-phenyl)-ethyl]-3-methyl-1,4,6,7-tetrahydro-pyrazolo[4,3-c]pyridin-5-yl}-N-methyl-2-phenyl-acetamide;

2-{4-[2-(4-Chloro-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;

2-{1,3-Dimethyl-4-[2-(4-trifluoromethyl-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(4-methyl-3-trifluoromethyl-phenyl)-ethyl]-1,4,6,7-tetrahydro-pyrazolo[4,3-c]pyridin-5-yl}-N-methyl-2-phenyl-acetamide;

2-[1-Ethyl-3-methyl-4-(2-m-tolyl-ethyl)-1,4,6,7-tetrahydro-pyrazolo[4,3-c]pyridin-5-yl]-N-methyl-2-phenyl-acetamide;

2-[1-Ethyl-3-methyl-4-(2-o-tolyl-ethyl)-1,4,6,7-tetrahydro-pyrazolo[4,3-c]pyridin-5-yl]-N-methyl-2-phenyl-acetamide;

2-{1-Butyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide;

2-{1-Ethyl-4-[2-(2-fluoro-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(3-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-3-trifluoromethyl-phenyl)-ethyl]-3-methyl-1,4,6,7-tetrahydro-pyrazolo[4,3-c]pyridin-5-yl}-N-methyl-2-phenyl-acetamide;

2-{1-Benzyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide;

2-{1-Ethyl-4-[2-(2-methoxy-phenyl)-ethyl]-3-methyl-1,4,6,7-tetrahydro-pyrazolo[4,3-c]pyridin-5-yl}-N-methyl-2-phenyl-acetamide;

N-Methyl-2-{3-methyl-1-phenethyl-4-[2-(4-trifluoromethyl-phenyl)-ethyl]-1,4,6,7-tetrahydro-pyrazolo[4,3-c]pyridin-5-yl}-2-phenyl-acetamide;

N-Methyl-2-{3-methyl-1-(2,2,2-trifluoro-ethyl)-4-[2-(4-trifluoromethyl-phenyl)-ethyl]-1,4,6,7-tetrahydro-pyrazolo[4,3-c]pyridin-5-yl}-2-phenyl-acetamide;

2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide;

2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(2-fluoro-3-methyl-phenyl)-ethyl]-3-methyl-1,4,6,7-tetrahydro-pyrazolo[4,3-c]pyridin-5-yl}-N-methyl-2-phenyl-acetamide;

2-{4-[2-(2,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(2,4-Difluoro-3-methyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-3-methyl-4-[2-(2,4,5-trifluoro-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(2,4,5-trifluoro-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(2,3,4-trifluoro-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(2-methyl-5-trifluoromethyl-phenyl)-ethyl]-1,4,6,7-tetrahydro-pyrazolo[4,3-c]pyridin-5-yl}-N-methyl-2-phenyl-acetamide;

2-{1-Ethyl-4-[2-(3-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide;

2-{4-[2-(3,5-Bis-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,5-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,5-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(2,3-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,4-Dichloro-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(2,6-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide; Out of this group of compounds, especially preferred compounds are:

2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide;

2-{4-[2-(2,3-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(4-ethyl-phenyl)-ethyl]-3-methyl-1,4,6,7-tetrahydro-pyrazolo[4,3-c]pyridin-5-yl}-N-methyl-2-phenyl-acetamide;

2-{4-[2-(3,5-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,5-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide;

The compounds of the general formula I and/or Ia are useful for the treatment and/or prevention of the diseases mentioned herein.

In one embodiment, the invention relates to a method for the treatment and/or prevention of the diseases mentioned herein, said method comprising administering to a subject a pharmaceutically active amount of a compound of general formula I and/or Ia.

A further aspect of the present invention relates to pharmaceutical compositions comprising a compound of formula I and/or Ia and a pharmaceutically acceptable carrier material. These pharmaceutical compositions may be used for the treatment or prevention of the above-mentioned diseases. The pharmaceutical compositions can be used for enteral, parenteral, or topical administration. They can be administered, for example, peroral, e.g. in the form of tablets, coated tablets, dragées, hard and soft gelatine capsules, solutions, emulsions or suspensions, nasal, e.g. in the form of sprays, rectal, e.g. in the form of suppositories, parenteral, e.g. in the form of injection solutions or infusion solutions, or topical, e.g. in the form of ointments, creams or oils.

The invention also relates to the use of a compound of general formula I and/or Ia for the preparation of pharmaceutical compositions for the treatment and/or prevention of the above-mentioned diseases.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of general formula I and/or Ia and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of general formula I and/or Ia or the above-mentioned pharmaceutical compositions may also be used in combination with one or more other therapeutically useful substances.

The present invention also relates to pro-drugs of a compound of general formula I and/or Ia that convert in vivo to the compound of general formula I and/or Ia as such. Any reference to a compound of general formula I and/or Ia is therefore to be understood as referring also to the corresponding pro-drugs of the compound of general formula I and/or Ia, as appropriate and expedient.

Compounds as described above have $IC_{50}$ values below 150 nM at least on one of the orexin receptors, which have been determined with the FLIPR (Fluorometric Imaging Plates Reader) method described in the experimental section. Preferred compounds are active against both, the $OX_1$ and $OX_2$ receptors.

The compounds according to formula (I) and/or (Ia) are useful in the preparation of a medicament for the prevention or treatment of diseases selected from the group consisting of dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions.

Compounds of formula (I) and/or (Ia) are particularly suitable for use in the treatment of diseases or disorders selected from the group consisting of eating or drinking disorders, all types of sleep disorders, or cognitive dysfunctions in the healthy population and in psychiatric and neurologic disorders. Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

Sleep disorders include all types of insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

The compounds of the general formula I and/or Ia of the present invention may be prepared according to the procedures described herein, especially as described in the experimental part.

The compounds according to general formula (I) and/or (Ia) are useful in the preparation of a medicament for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; postoperative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid haemorrhage, ischemic and hemorrhagic stroke and vascular dementia; chronic renal failure and other renal diseases; gout; kidney cancer; urinary incontinence; and other diseases related to general orexin system dysfunctions.

Compounds of general formula (I) and/or (Ia) are particularly suitable for use in the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders. Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders. In a further preferred embodiment of the invention compounds of general formula (I) and (Ia) are particularly suitable for use in the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of general formula (I) and/or (Ia) are particularly suitable for use in the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of general formula (I) and/or (Ia) are particularly suitable for use in the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of general formula (I) and/or (Ia) are particularly suitable for use in the treatment of diseases or disorders selected from the group consisting of psychoactive substance use and abuse that comprise all types of psychological or physical addictions and their related tolerance and dependence components.

General Methods for the Preparation of Compounds of General Formula I and/or Ia:

aldehyde-derivative D under Pictet-Spengler conditions and microwave irradiation to give precursor E which can be N-alkylated by compounds F to give final orexin receptor antagonists G. In case Y shall represent —$CH_2$— or —$CH_2$—O— in the final compounds G, the intermediate C is reacted

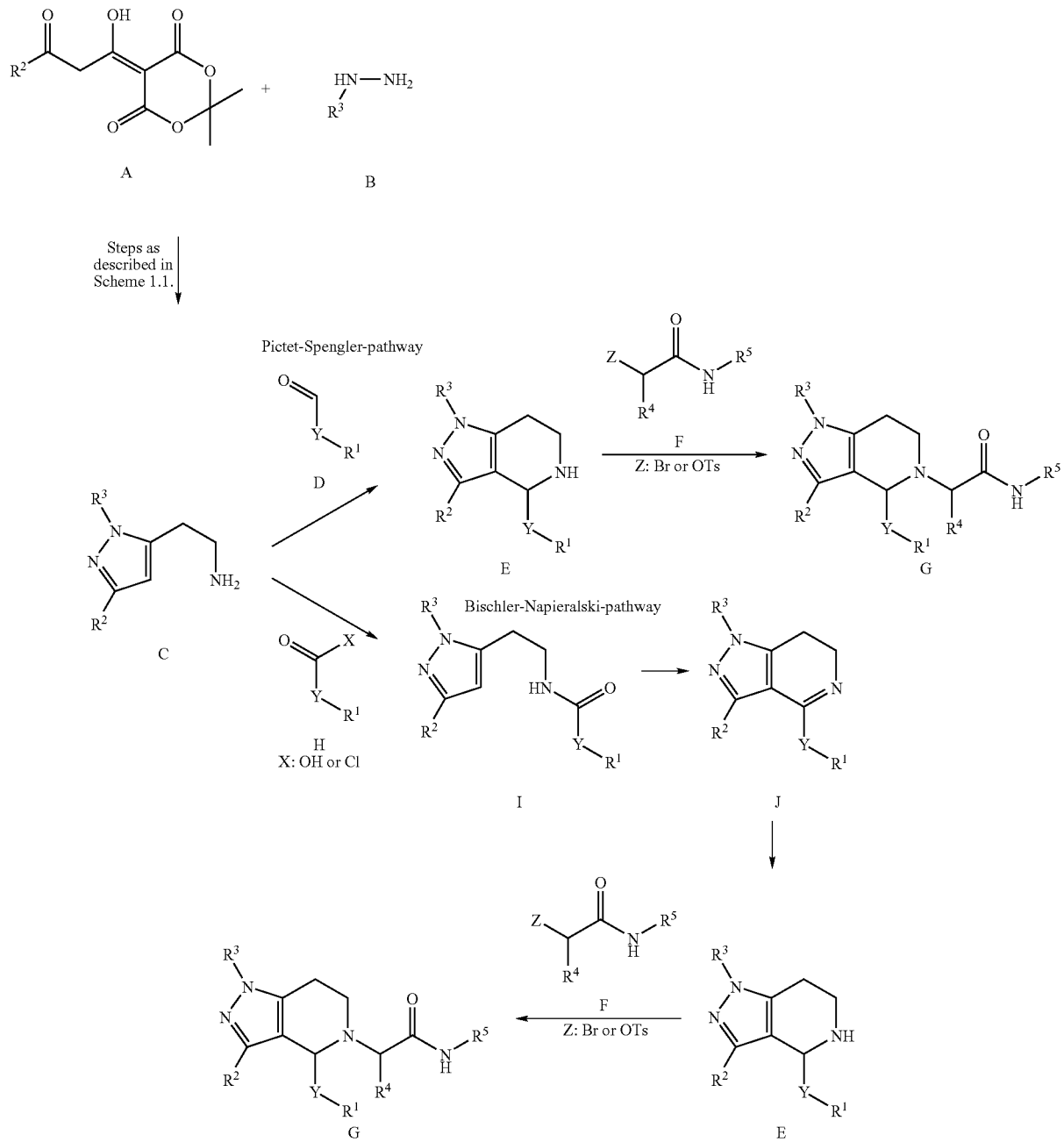

$R^1$, $R^2$, $R^3$, $R^4$, $R^5$ and Y are as defined in general formula I above, X represents OH or Cl and Z represents Br or OTs; The preparation of an example for intermediates F is descirbed in WO05/118548.

Intermediate A is reacted with the unsymmetrical hydrazine B to give via a 6-step sequence (see experimental part) the 2,5-di-substituted pyrazole-3-yl-ethylamine C in a regioselective manner. In case Y shall represent —$CH_2$—$CH_2$— in the final compounds, the intermediate C is reacted with an with carboxylic acid derivatives under amide-bond forming conditions to give the amide-intermediates I which are transformed to the cyclic imines J under Bischler-Napieralski conditions followed by imine reduction to give the amine precursors E. By N-alkylation with derivatives F, the final orexin receptor antagonists G could be obtained. (The Bischler-Napieralski pathway is as well suitable for the preparation of compounds wherein Y represents —CH$_2$—CH$_2$—; The Pictet-Spengler pathway is not suitable for the preparation of compounds wherein Y represents —CH$_2$— or —CH$_2$—O— as the aldehyde intermediates D comprising these structural features are not stable enough to react via the desired pathway under the conditions applied in the Pictet-Spengler reaction to prepare intermediates E).

The compounds of the formula A, B, D, F and H are either commercially available, or can be synthesized according to methods known in the art.

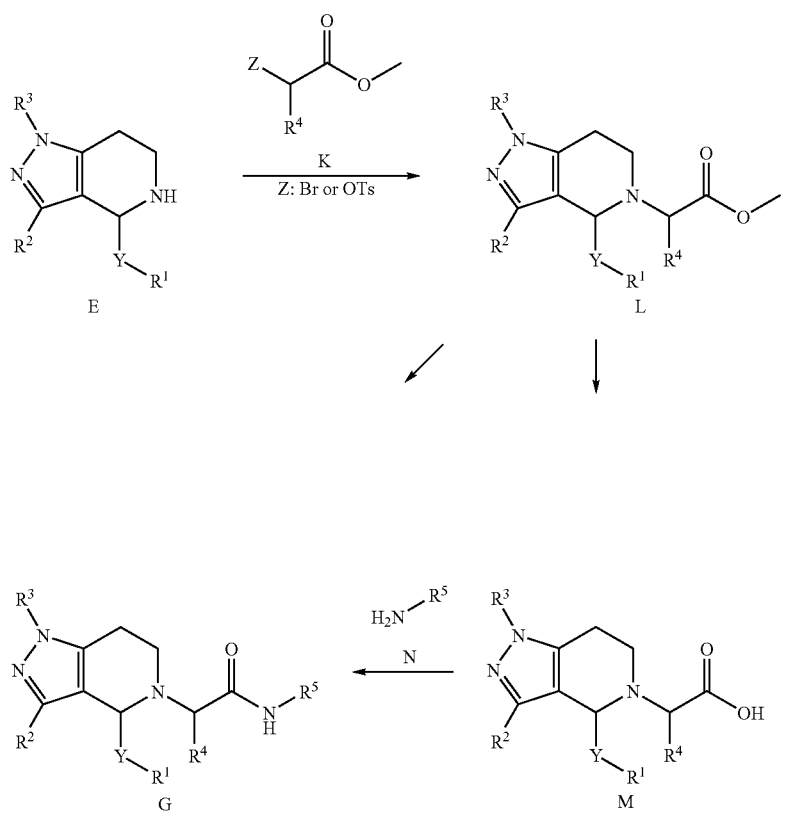

R$^1$, R$^2$, R$^3$, R$^4$, R$^5$ and Y are as defined in general formula I above, X represents OH or Cl and Z represents Br or OTs; For general methods see also WO 00/168609 and WO 02/051838 and WO 04/085403

In a slightly different route the intermediate E is reacted with ester derivatives K (instead of amide derivatives F) to give intermediate L, which can either be directly transformed into the final compounds G by reacting the ester with an amine derivative N or which can first be hydrolyzed to the acid intermediate M followed by reaction with an amine N to give final compounds G.

The compounds of the formula N and K are either commercially available, or can be synthesized according to methods known in the art.

In general, all chemical transformations can be performed according to well-known standard methodologies as described in the literature or as described in the procedures below.

Preparation of Compounds of General Formula I and/or Ia:
Scheme 1.1: Synthesis of pyrazole precursors
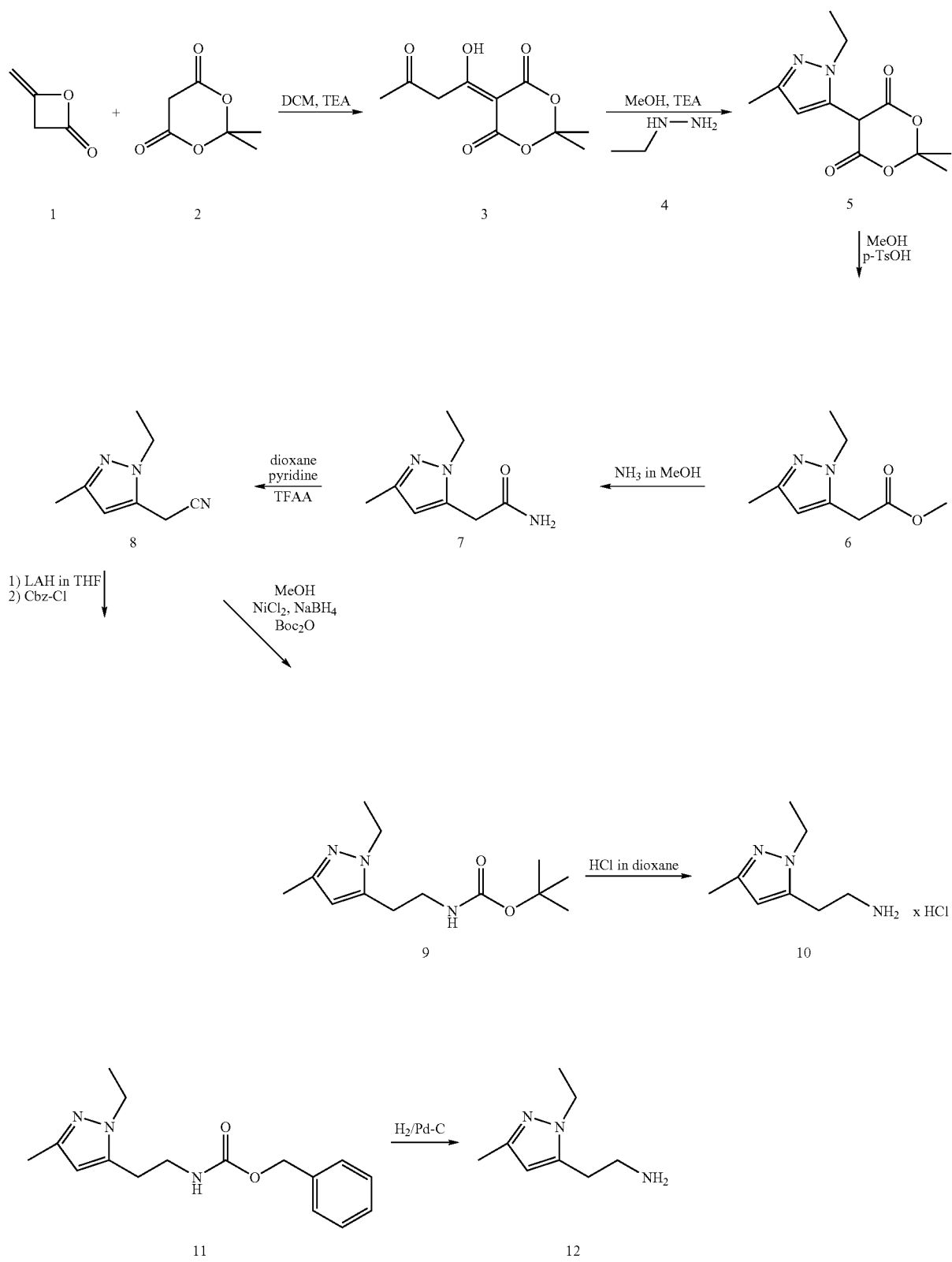

The preparation of the pyrazole-3-yl-ethylamine-derivatives started by the coupling of diketene (1) and Meldrum's acid (2) in a solvent like DCM in the presence of a base like TEA to give after acidc work-up the intermediate 3. Reaction of compound 3 with an appropriate hydrazine derivative (e.g. ethylhydrazine (4)) in solvent like methanol in the presence of a base like TEA resulted in the formation of the pyrazole-derivative 5. Hydrolysis under acidic conditions (with e.g. p-TsOH in methanol) resulted in the formation of the methylester 6 which was efficiently transformed to the primary amide 7 by stirring it in methanolic ammonia (7M) for 20 h. Dehydration of 7 to prepare the nitrile 8 was accomplished by reaction with TFAA in dioxane in the presence of pyridine. Reduction of the nitrile 8 to the Boc-protected pyrazole-3-yl-ethylamine-derivative 9 was accomplished by the use of sodium-borohydride and catalytic amounts of Nickel (II)-chloride in methanol in the presence of Boc$_2$O. Deprotection to the free amine hydrochloride was achieved via a standard procedure with 4M HCl in dioxane to give, after suspending it in diethylether, filtering and drying, 10 as a white powder. In order to obtain the free amine 12, the nitrile precursor 8 was reduced to the amine-intermediate by LAH. After work-up according to the "Corey-proceudre" the crude product was dissolved in a mixture of diethylether/THF followed by the addition of an aqueous base (e.g. 1M sodium bicarbonate) and benzyl chloroformiate to give the Cbz-protected amine 11 which could then be purified by column chromatography and after purification deprotected by hydrogenolysis to give the desired compound 12. Whether compound 10 or compound 12 were prepared was dependent on the subsequent transformations intended.

Scheme 1.2: Preparation of 2-substituted 5-methyl-pyrazol-3-yl-ethylamines

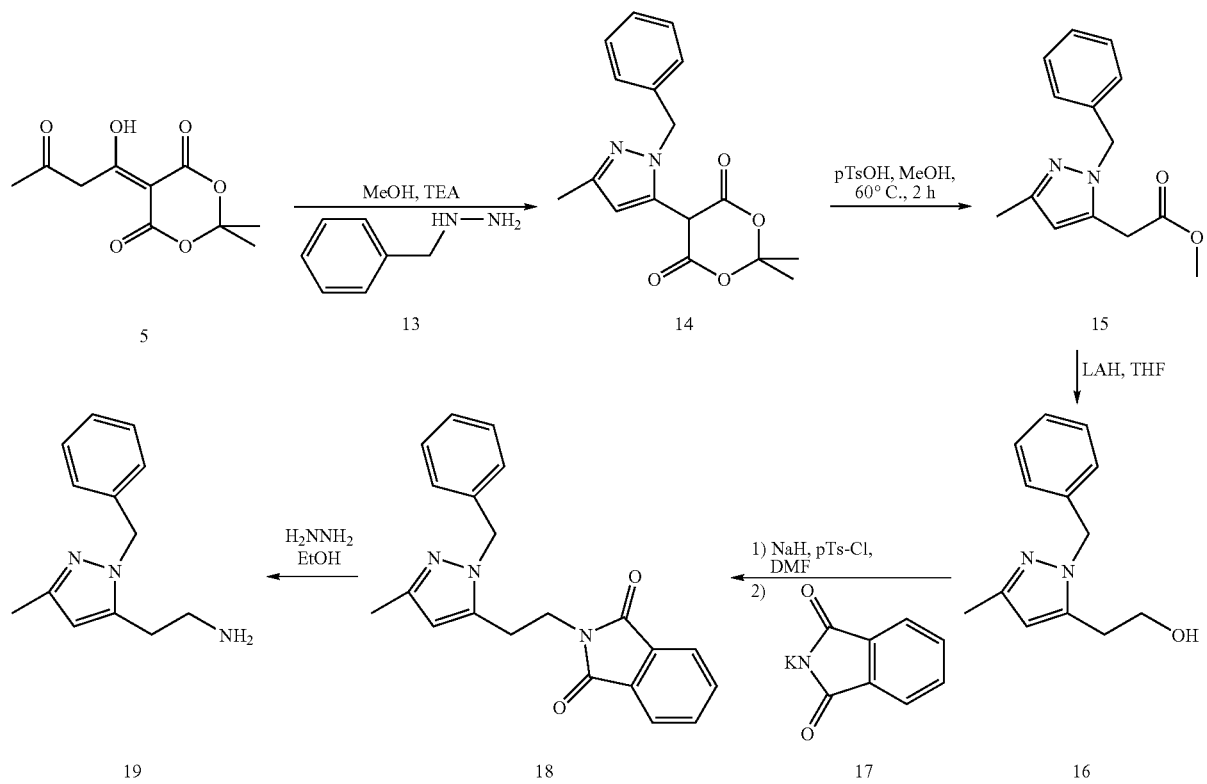

The following compounds were prepared along the same sequence:

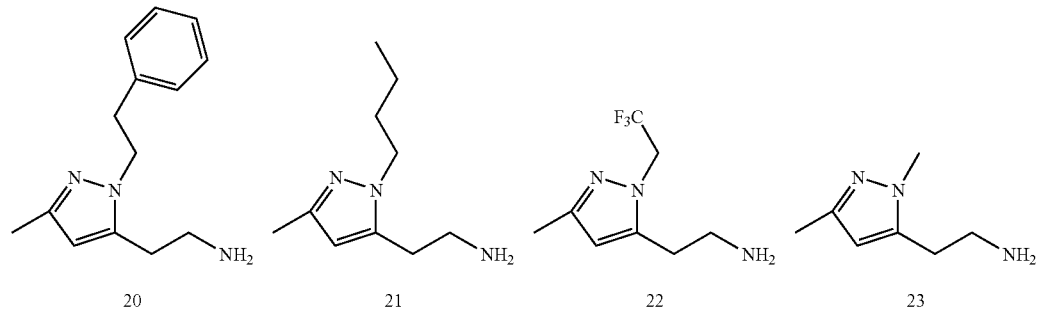

Scheme 1.2 summarizes the preparation of further regioselectively unsymmetrically substituted pyrazole-3-yl-ethylamines. The synthesis again starts from the regioselective condensation of precursor 5 with an unsymmetrical hydrazine-derivative (e.g. benzylhydrazine 13) to give the pyrazole-intermediate 14 which after hydrolysis/decarboxylation resulted in the ester 15. Reduction of the ester 15 with LAH gave the alcohol 16, which after deprotonation with sodium hydride in DMF was transformed into the tosylate-intermediate and followed by the addition of potassium phthalimide (Gabriel synthesis) to give the amine-precursor 18. Hydrazine cleavage of the phthalimide resulted in the formation of the 2-benzyl substituted pyrazole-3-yl-ethylamine derivative 19. Compounds 20 to 23 were prepared according to the same sequence of transformations.

Scheme 2: Preparation of substituted 3-phenyl-propionaldehyde precursors

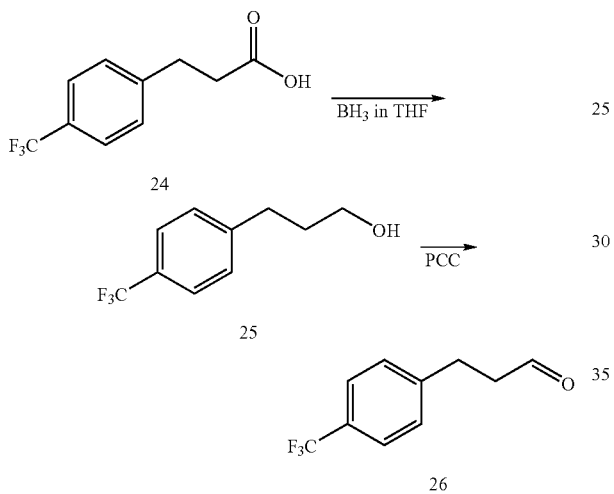

According to this 2 step procedure the following phenyl-propanal derivatives were prepared:

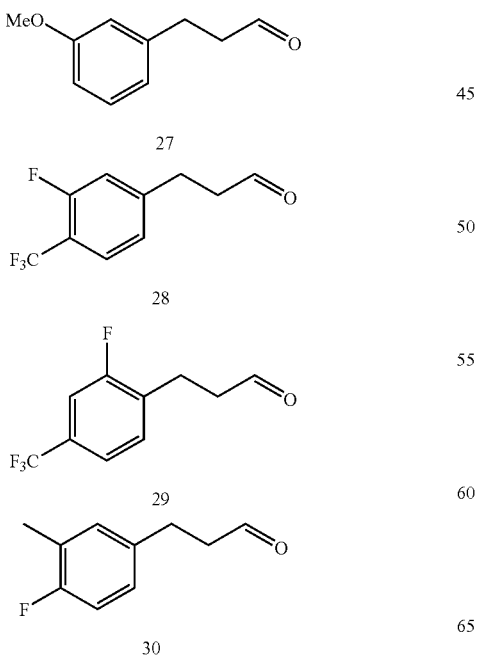

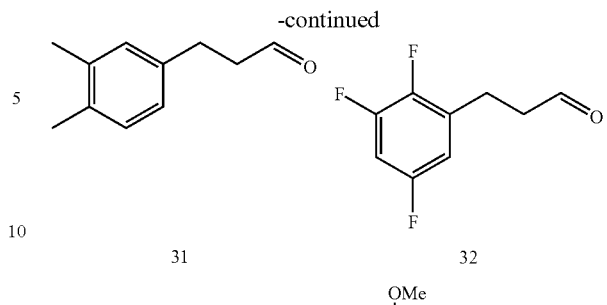

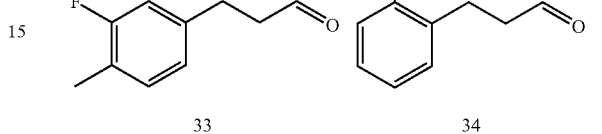

In case the hydrocinnamic acid derivatives were commercially available the 3-phenyl-propionaldehydes were prepared by the two step sequence depicted in Scheme 2; e.g. 4-trifluoromethyl-hydrocinnamic acid (24) was reduced to the 3-(4-Trifluoromethyl-phenyl)-propan-1-ol (25) according to standard protocols with borane in THF (1M). Oxidation to the aldehyde 26 was achieved by PCC in DCM according to a standard protocol developed by Corey et al. The substituted 3-phenyl-propionaldehydes 27 to 39 were synthesized according to the exact same procedure. Due to the fact that the 3-phenylpropananal-compounds were only of limited stability, they were usually prepared just before their use in the subsequent Pictet-Spengler-reaction.

Scheme 3: Preparation of substituted phenyl-propionaldehydes

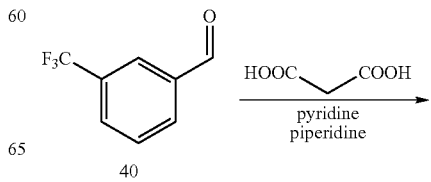

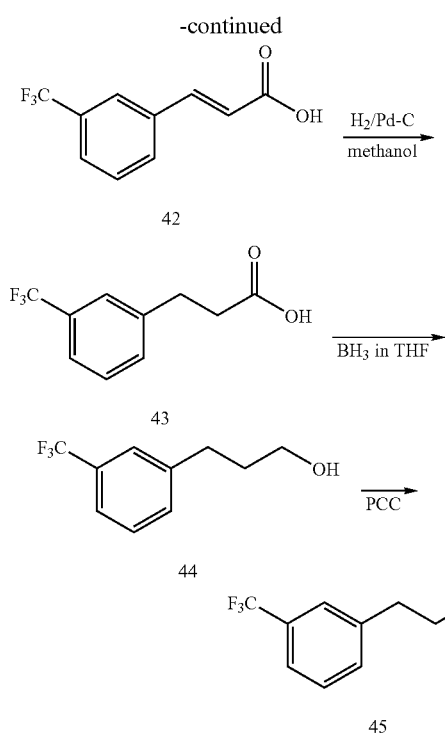
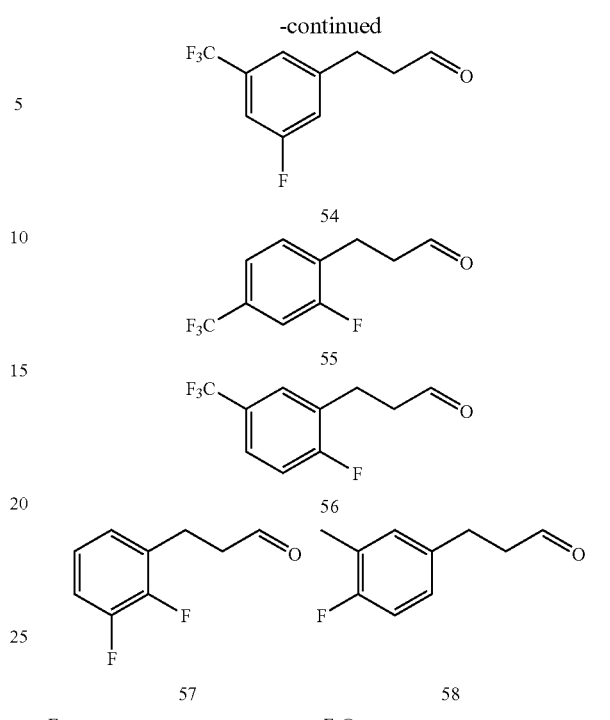

The following compounds were prepared according to the same sequence:

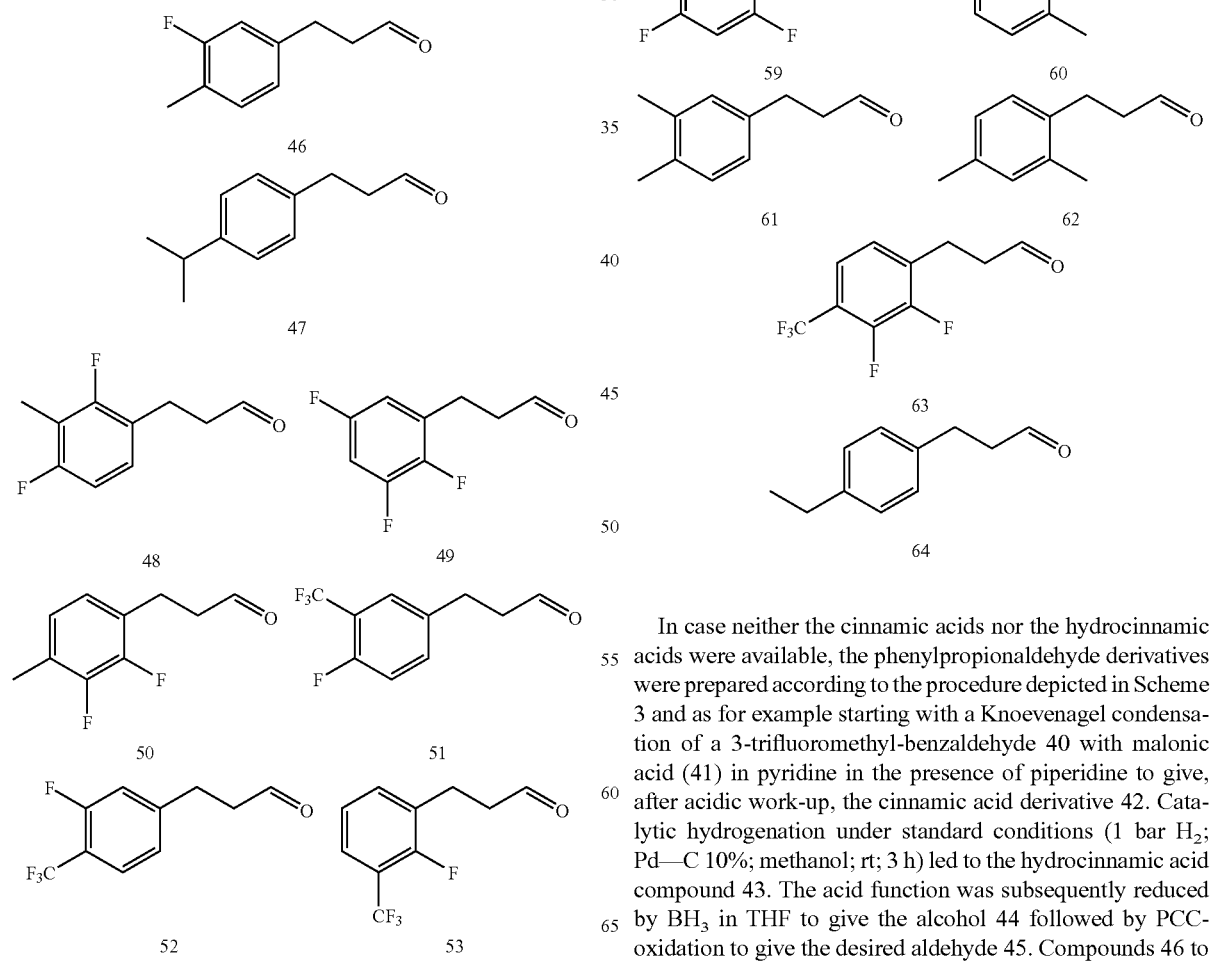

In case neither the cinnamic acids nor the hydrocinnamic acids were available, the phenylpropionaldehyde derivatives were prepared according to the procedure depicted in Scheme 3 and as for example starting with a Knoevenagel condensation of a 3-trifluoromethyl-benzaldehyde 40 with malonic acid (41) in pyridine in the presence of piperidine to give, after acidic work-up, the cinnamic acid derivative 42. Catalytic hydrogenation under standard conditions (1 bar $H_2$; Pd—C 10%; methanol; rt; 3 h) led to the hydrocinnamic acid compound 43. The acid function was subsequently reduced by $BH_3$ in THF to give the alcohol 44 followed by PCC-oxidation to give the desired aldehyde 45. Compounds 46 to 64 can be prepared according to the same synthetic sequence.

Scheme 4: Preparation of further substituted phenyl-propionaldehydes

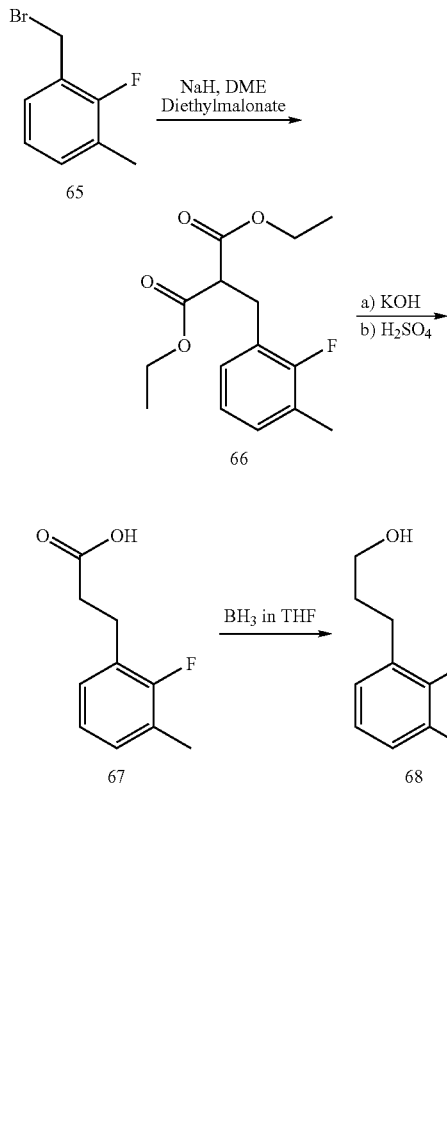

The following compounds were prepared according to the same sequence:

70    71

Scheme 5: Synthesis of final compounds (e.g. Example 1)

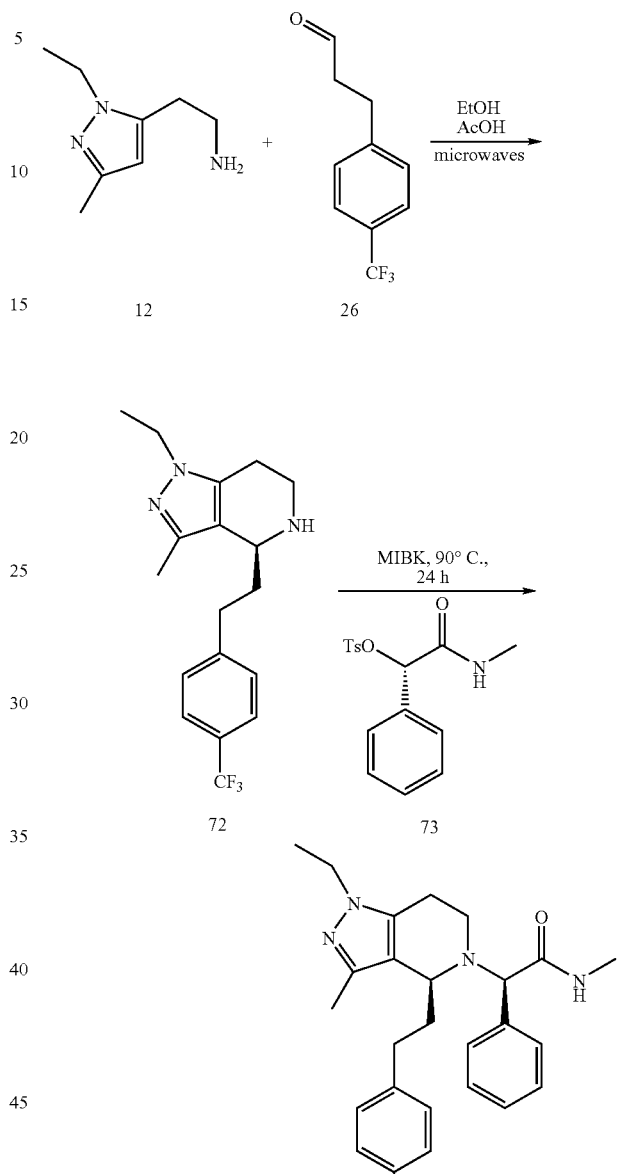

74
Example 1

In Scheme 4 an alternative pathway for the preparation of substituted phenylpropionylaldehydes is depicted. 2-Fluoro-3-methylbenzylbromide (65) is reacted with diethylmalonate to give intermediate 66. Esterhydrolysis under basic conditions followed by decarboxylation under acidic conditions resulted in the hydrocinnamic acid intermediate 67. Subsequent borane-reduction (→alcohol 68) and PCC-oxidation led to the desired substituted phenyl-propionaldehyde 69. Compounds 70 and 71 can be prepared according to the same synthetic sequence.

Scheme 5 summarizes the sequence applied for the preparation of 4-"phenethyl"-substituted examples. For example the pyrazol-ethylamine derivative 12 can be reacted with the phenyl-propionaldehyde 26 in ethanol in the presence of 2 equivalents of acetic acid in the microwave oven for 6 minutes (100 Watt; 130° C., 14 bar) to give after HPLC purification the secondary amine-intermediates 72. $S_N2$-reaction with the tosylate 73 (described in WO 2005/118548) in methyl-isobutyl-ketone at 90° C. for 24 h under inert conditions led to the final compound 74 (Example 1). Examples 2 to 42 could be prepared according to the sequence described in Scheme 5.

The following examples illustrate the invention but do not limit the scope thereof. All temperatures are stated in ° C.

| Abbreviations (as used herein) | |
|---|---|
| aq. | aqueous |
| Boc | tert.-butyloxycarbonyl |
| DCM | dichloromethane |
| DMF | dimethylformamide |
| DMSO | dimethylsulfoxide |
| EDC | N-(3-dimethylaminopropyl)-N'-ethyl-carbodiimid |
| ELSD | Evaporative Light-Scattering Detection |
| Et | ethyl |
| EtOAc | ethyl acetate |
| h | hour(s) |
| HPLC | High Performance Liquid Chromatography |
| HV | High Vacuum |
| LAH | lithium aluminumhydride |
| LC-MS | Liquid Chromatography - Mass Spectroscopy |
| min | minute(s) |
| MS | Mass Spectroscopy |
| PBS | phosphate buffered saline |
| PyBOP | benzotriazole-1-yl-oxy-tris-pyrrolidino-phosphonium hexafluorophosphate |
| PCC | pyridinium chlorochromate |
| p-TsOH | para-toluenesulfonic acid |
| rt | room temperature |
| sat. | saturated |
| TBTU | O-benzotriazol-1-yl-N,N,N',N'-tetramethyluronium tetrafluoroborate |
| TEA | triethylamine |
| TFA | trifluoroacetic acid |
| TFAA | trifluoroacetic anhydride |
| THF | tetrahydrofurane |
| TLC | Thin Layer Chromatography |
| $t_R$ | retention time |
| UV | ultra violet |
| Vis | visible |

GENERAL PROCEDURES AND EXAMPLES

HPLC Conditions

Analytic: Zorbax 59 SB Aqua column, 4.6×50 mm from Agilent Technologies. Eluents: A: acetonitrile; B: H$_2$O+0.5% TFA. Gradient: 90% B→5% B over 2 min. Flow: 1 mL/min. Detection: UV/Vis+MS.

Preparative: Zorbax SB Aqua column, 20×500 mm from Agilent Technologies. Eluent: A: Acetonitrile; B: H$_2$O+0.05% ammonium hydroxide (25% aq.). Gradient: 80% B→10% B over 6 min. Flow: 40 mL/min. Detection: UV+MS, or UV+ELSD.

Chiral, analytic: Regis Whelk column, 4.6×250 mm, 10 µm. Eluent A: EtOH+0.05% Et$_3$N. Eluent B: hexane. Isocratic conditions, usually 60% B, over 40 min, 1 mL/min. The isocratic mixture may vary, depending on the compounds.

Chiral, preparative: As analytical conditions, but on a Regis Whelk 01 column, 50×250 mm and a flow of 100 mL/min.

Preparation of Precursors and Intermediates:

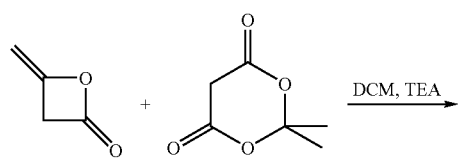

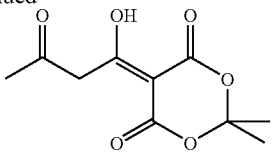

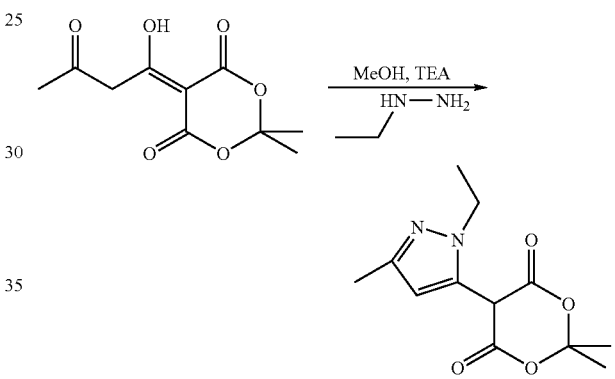

In an inert atmosphere, meldrum's acid (50 g, 347 mmol) was dissolved in DCM (300 ml) and TEA (35.1 g, 347 mmol) was added. The resulting mixture was cooled to 0° C. followed by drop by drop addition of diketene (35 g, 416.3 mmol). The reaction mixture was stirred for 2 h at r.t. cooled again to 0° C. and 1 M hydrochloric acid solution (700 ml) was slowly added. The layers were separated and the organic layer was dried over magnesium sulfate, filtered and concentrated under reduced pressure to give 79.36 g (quantitative yield) of the product 5-(1-hydroxy-3-oxo-butylidene)-2,2-dimethyl-[1,3]dioxane-4,6-dione as an orange solid. LC-MS: $t_R$=0.55 min; [M+H]$^+$=no ionisation.

5-(1-Hydroxy-3-oxo-butylidene)-2,2-dimethyl-[1,3]dioxane-4,6-dione (10 g, 44 mmol) was dissolved in anhydrous methanol (140 ml) and cooled to 0° C. followed by drop by drop addition of a solution of ethylhydrazine oxalate (7.24 g, 48.2 mmol) and TEA (9.75 g, 96.4 mmol) in anhydrous methanol (60 ml) with the help of a dropping funnel within 15 minutes. Upon completion of the addition, the mixture was slowly warmed to 60° C. and stirring was continued for 90 minutes. The reaction mixture was concentrated to dryness under reduced pressure and further dried at HV for 15 minutes to give 11.5 g (quantitative yield) of the product 5-(2-ethyl-5-methyl-2H-pyrazol-3-yl)-2,2-dimethyl-[1,3]dioxane-4,6-dione as an orange oil which was used in the next step without further purification. LC-MS: $t_R$ 0.52 min; [M+H]$^+$=no ionisation.

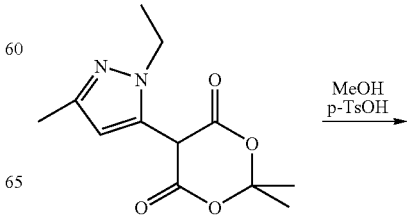

-continued

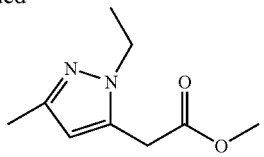

5-(2-Ethyl-5-methyl-2H-pyrazol-3-yl)-2,2-dimethyl-[1,3]dioxane-4,6-dione (11.05 g, 43.8 mmol) was dissolved in anhydrous methanol (125 ml) followed by the addition of p-TsOH×H₂O (36.68 g, 192.85 mmol). The resulting reaction mixture was heated to 60° C. for 75 minutes, cooled to 0° C. and triethylamine (26.85 ml, 192.9 mmol) was added drop by drop over a period of 20 minutes. The resulting mixture was concentrated under reduced pressure. The residue was taken into DCM (200 ml) and washed with water (2×75 ml), dried over magnesium sulfate, filtered and concentrated under reduced pressure. The crude product was purified by flash chromatography (silicagel, DCM/methanol=30/1) to give 5.56 g (70%) of (2-ethyl-5-methyl-2H-pyrazol-3-yl)-acetic acid methyl ester. LC-MS: $t_R$ 0.62 min; [M+H]⁺=183.18.

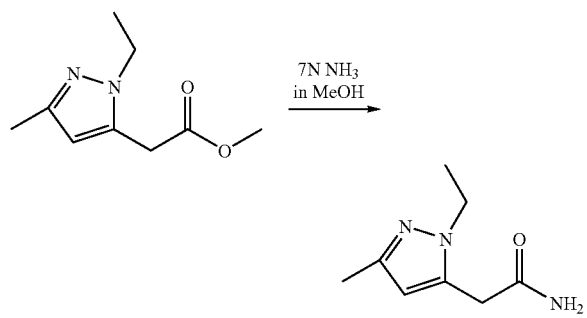

(2-Ethyl-5-methyl-2H-pyrazol-3-yl)-acetic acid methyl ester (4.64 g, 25.46 mmol) was dissolved in 7N ammonia in methanol (100 ml, 700 mmol NH₃). The reaction mixture was stirred at rt for 20 h. The solvent was removed under reduced pressure to give 4.25 g (quant. yield) of 2-(2-ethyl-5-methyl-2H-pyrazol-3-yl)-acetamide. LC-MS: $t_R$=0.33 min; [M+H]⁺= no ionisation.

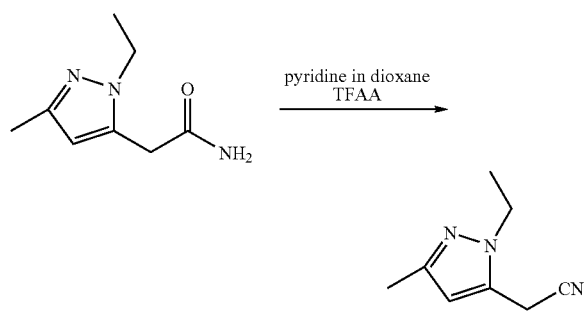

2-(2-Ethyl-5-methyl-2H-pyrazol-3-yl)-acetamide (2.0 g, 11.96 mmol) was dissolved in dioxane (180 ml) followed by the addition of pyridine (1.89 g, 23.9 mmol). The resulting solution was cooled to 0° C. and TFM (2.76 g, 13.16 mmol) was added drop by drop. The suspension was then slowly warmed to rt and stirring was continued in total for 4 h. The volatiles were removed under reduced pressure, the residue was dissolved in DCM (150 ml), washed with water (2×100 ml), dried over magnesium sulfate, filtered and concentrated under reduced pressure. After flash-chromatography (silicagel; DCM/methanol=40/1), 1.58 g (88%) of (2-ethyl-5-methyl-2H-pyrazol-3-yl)-acetonitrile was obtained. LC-MS: $t_R$=0.65 min; [M+H]⁺=150.18.

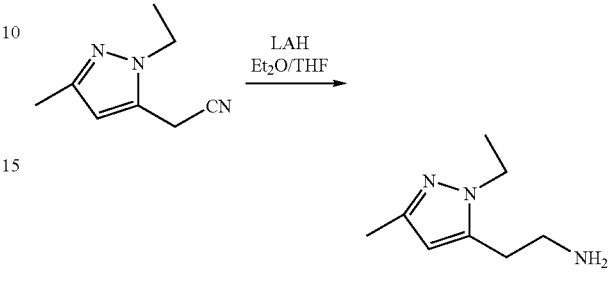

LAH (806 mg, 21.22 mmol) was suspended in anhydrous diethylether (105 ml) at 0° C. in an inert atmosphere. (2-Ethyl-5-methyl-2H-pyrazol-3-yl)-acetonitrile (1.58 g, 10.6 mmol) dissolved in diethylether (10 ml) was added dropwise at 0° C. over a period of 11 minutes followed by the addition of anhydrous THF (115 ml). Stirring was continued for 2.5 h followed by careful addition of water (0.8 ml), 15% aqueous sodium hydroxide solution (0.8 ml) and water (2.4 ml). Stirring was continued at rt for 10 minutes. The mixture was filtered, the filter cake was washed with diethylether and the filtrate was concentrated under reduced pressure. The crude 2-(2-ethyl-5-methyl-2H-pyrazol-3-yl)-ethylamine was further transformed to the Z-protected amine in the next step without prior purification. LC-MS: $t_R$=0.2 min (broad peak); [M+H]⁺=no ionization.

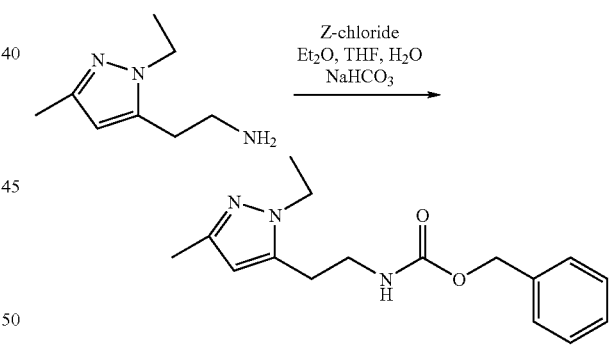

The crude primary amine 2-(2-ethyl-5-methyl-2H-pyrazol-3-yl)-ethylamine (theoretical amount: 1.62 g, 10.6 mmol) was dissolved in diethylether (115 ml), THF (115 ml) and water (55 ml) at 0° C. followed by the addition of sodium bicarbonate (2.22 g, 26.5 mmol) and drop by drop addition of benzyl chloroformate (1.99 g, 11.7 mmol). Stirring was continued for 30 min. The layers were separated and the aqueous layer was extracted with diethylether (55 ml). The combined organic layers were dried over magnesium sulfate, filtered and concentrated under reduced pressure. Purification was accomplished by flash chromatography (DCM/methanol=50/1) to give 881 mg (29%) of [2-(2-ethyl-5-methyl-2H-pyrazol-3-yl)-ethyl]-carbamic acid benzyl ester. LC-MS: $t_R$=0.76 min; [M+H]⁺=288.24.

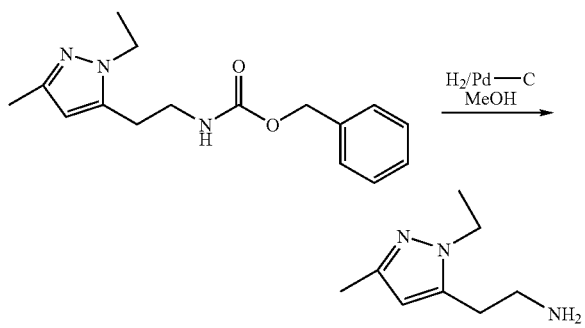

[2-(2-Ethyl-5-methyl-2H-pyrazol-3-yl)-ethyl]-carbamic acid benzyl ester (818 mg, 2.85 mmol) was dissolved in methanol (8 ml) and added to a suspension of Pd—C (10%, 163 mg) in methanol (8 ml), put under an atmosphere of hydrogen (1 bar) and stirring at rt was continued for 45 minutes. The reaction mixture was filtered over a pad of celite and the filtrate was concentrated under reduced pressure to give 408 mg (93.7%) of 2-(2-Ethyl-5-methyl-2H-pyrazol-3-yl)-ethylamine. LC-MS: $t_R$=0.20 min, broad peak; [M+H]$^+$= no ionization.

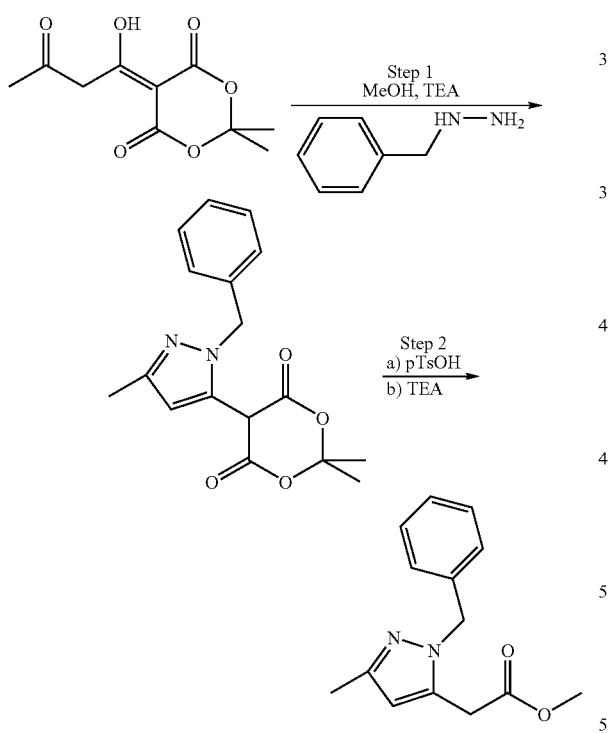

Step 1:

5-(1-Hydroxy-3-oxo-butylidene)-2,2-dimethyl-[1,3]dioxane-4,6-dione (1 g, 4.4 mmol) was dissolved in anhydrous methanol (8.1 ml) and cooled to 0° C. followed by the addition of a solution of benzylhydrazine dihydrochloride (885 mg, 4.4 mmol) and TEA (979 mg, 9.7 mmol) in anhydrous methanol (6 ml). The reaction mixture was heated to 60° C. for 2 h. Product was detected by LC-MS. Step 2 was performed without any prior work-up. LC-MS: $t_R$=0.66 min; [M+H]$^+$=315.4.

Step 2:

To the solution of 5-(2-benzyl-5-methyl-2H-pyrazol-3-yl)-2,2-dimethyl-[1,3]dioxane-4,6-dione obtained in step 1, pTsOH (3.74 g, 19.4 mmol) was added and stirring was continued for 2 h at 60° C. The reaction mixture was cooled to 0° C. and TEA (1.96 g, 19.4 mmol) was added drop by drop. Stirring was continued for 15 minutes. The mixture was concentrated under reduced pressure, the residue taken up into DCM (30 ml), washed with water (2×15 ml), dried over magnesium sulfate, filtered and concentrated under reduced pressure to give 1.03 g (96%) of (2-benzyl-5-methyl-2H-pyrazol-3-yl)-acetic acid methyl ester which was used in the next step without further purification. LC-MS: $t_R$=0.83 min; [M+H]$^+$=245.16.

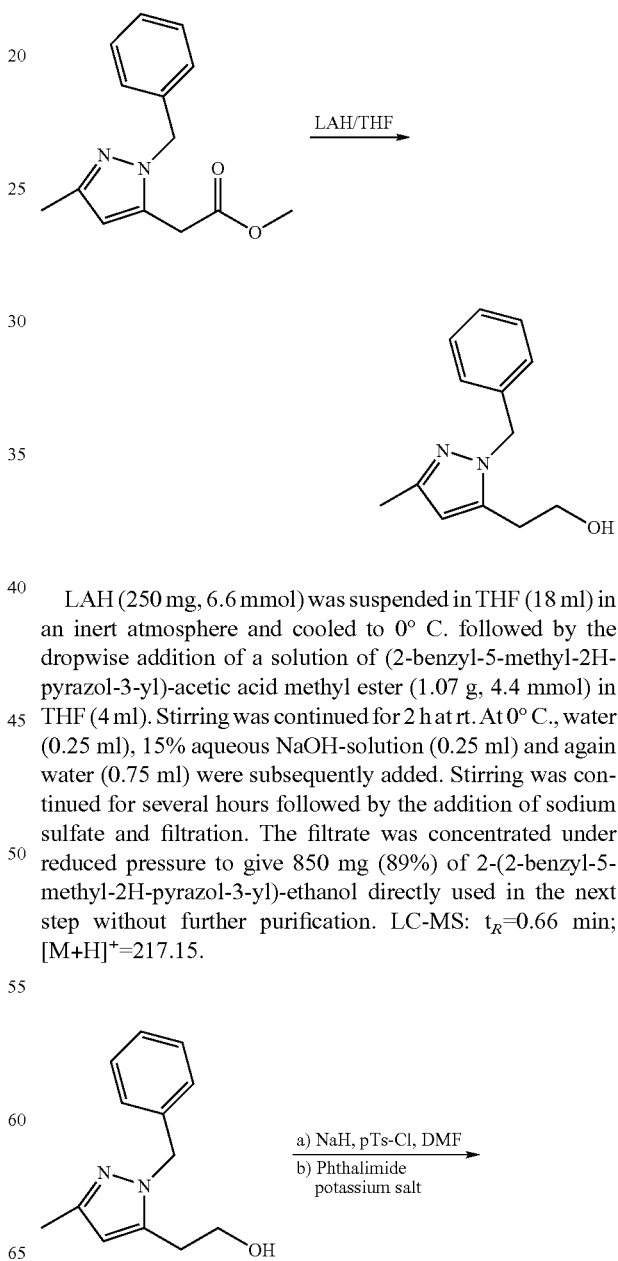

LAH (250 mg, 6.6 mmol) was suspended in THF (18 ml) in an inert atmosphere and cooled to 0° C. followed by the dropwise addition of a solution of (2-benzyl-5-methyl-2H-pyrazol-3-yl)-acetic acid methyl ester (1.07 g, 4.4 mmol) in THF (4 ml). Stirring was continued for 2 h at rt. At 0° C., water (0.25 ml), 15% aqueous NaOH-solution (0.25 ml) and again water (0.75 ml) were subsequently added. Stirring was continued for several hours followed by the addition of sodium sulfate and filtration. The filtrate was concentrated under reduced pressure to give 850 mg (89%) of 2-(2-benzyl-5-methyl-2H-pyrazol-3-yl)-ethanol directly used in the next step without further purification. LC-MS: $t_R$=0.66 min; [M+H]$^+$=217.15.

-continued

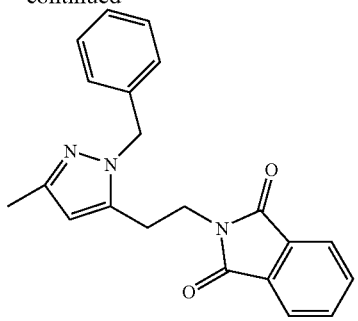

2-(2-Benzyl-5-methyl-2H-pyrazol-3-yl)-ethanol (848 mg, 3.92 mmol) was dissolved in DMF (21 ml) and cooled to −20° C. followed by the addition of sodium hydride (218 mg, 5.02 mmol). Stirring was continued at rt for 30 minutes. The reaction mixture was again cooled to −20° C. and toluene-4-suofonyl chloride (pTs-Cl, 966 mg, 5.02 mmol) was added. The cooling bath was removed and stirring was continued for 2 h at rt and 30 minutes at 50° C. followed by the addition of potassium phthalimid (1.7 g, 9.2 mmol). Stirring at 50° C. was continued for 2 h. The reaction mixture was filtered and the filtrate was concentrated under reduced pressure. The residue was taken up in DCM (30 ml) filtered again and the filtrate was washed with water (30 ml). The phases were separated. The organic phase was dried over magnesium sulfate, filtered and concentrated under reduced pressure. The crude material was purified by preparative HPLC to give 80 mg (6%) of 2-[2-(2-benzyl-5-methyl-2H-pyrazol-3-yl)-ethyl]-isoindole-1,3-dione. LC-MS: $t_R$=0.95 min; $[M+H]^+$=346.31.

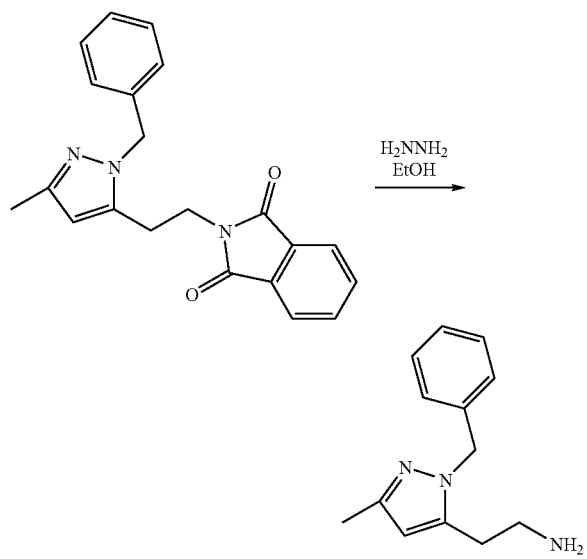

2-[2-(2-benzyl-5-methyl-2H-pyrazol-3-yl)-ethyl]-isoindole-1,3-dione (80 mg, 0.233 mmol) was dissolved in ethanol (2 ml) followed by the addition of an 1M solution of hydrazine in methanol (0.34 ml, 0.34 mmol). The reaction mixture was stirred at 90° C. for 16 h, cooled to rt and DCM (3 ml) was added and the suspension was filtered. The filtrate was concentrated under reduced pressure to give 40 mg (80%) 2-(2-benzyl-5-methyl-2H-pyrazol-3-yl)-ethylamine. LC-MS: $t_R$=0.58 min; $[M+H]^+$=216.38.

According to the procedure described above for the preparation of 2-(2-benzyl-5-methyl-2H-pyrazol-3-yl)-ethylamine, the following four derivatives could be prepared:

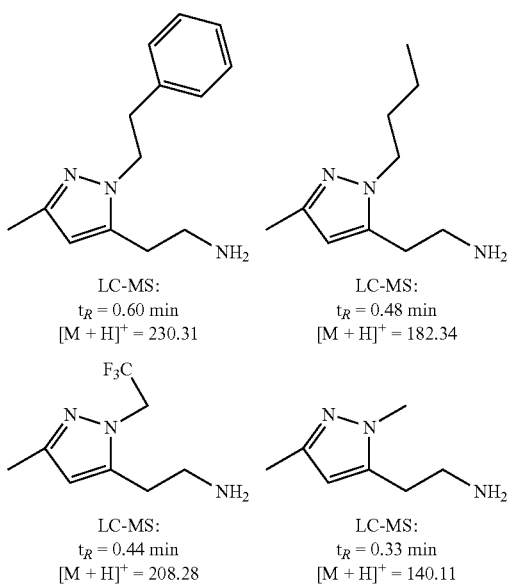

LC-MS:
$t_R$ = 0.60 min
$[M + H]^+$ = 230.31

LC-MS:
$t_R$ = 0.48 min
$[M + H]^+$ = 182.34

LC-MS:
$t_R$ = 0.44 min
$[M + H]^+$ = 208.28

LC-MS:
$t_R$ = 0.33 min
$[M + H]^+$ = 140.11

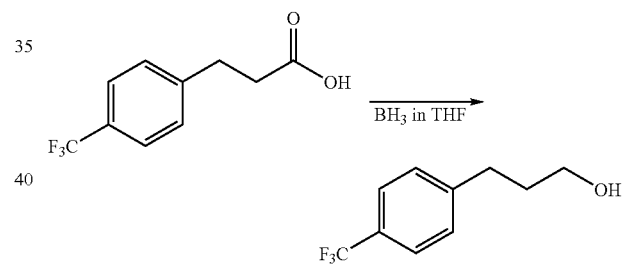

In an inert atmosphere, 3-(4-Trifluoromethyl-phenyl)-propionic acid (10 g, 45.8 mmol) was dissolved in anhydrous THF (250 ml) and cooled to 0° C. followed by the addition of a 1 M solution of borane in THF (69 ml, 69 mmol). Stirring was continued at 0° C. for 1 h and 16 h at rt followed by slow addition of methanol (100 ml) and water (100 ml). The organic solvents were evaporated under reduced pressure. The remaining water phase was extracted with DCM (3×100 ml) and the combined organic layers were washed with brine (100 ml), dried over magnesium sulfate, filtered and concentrated in vacuo. The crude residue was purified by flash chromatography (silicagel, DCM/methanol=9/1 to give 9.25 g (99%) of 3-(4-Trifluoromethyl-phenyl)-propan-1-ol. LC-MS: $t_R$=0.89 min; $[M+H]^+$=no ionisation.

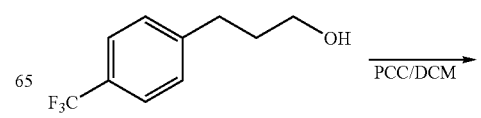

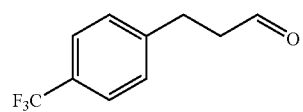

In an inert atmosphere, 3-(4-trifluoromethyl-phenyl)-propan-1-ol (1.02 g, 5 mmol) was dissolved in DCM (10 ml) and slowly added to a suspension of PCC (1.61 g, 7.5 mmol) in anhydrous DCM (15 ml). Stirring was continued for 4 h at rt. Anhydrous heptane (10 ml) was added to the reaction mixture followed by filtration over a pad of silicagel (15 g). The filtrate was evaporated to give 850 mg of 3-(4-trifluoromethyl-phenyl)-propionaldehyde. LC-MS: $t_R$=0.94 min; $[M+H]^+$=no ionisation.

According to the procedure described for the preparation of 3-(4-trifluoromethyl-phenyl)-propionaldehyde, the following substituted 3-phenyl-propionaldehyde derivatives were prepared:

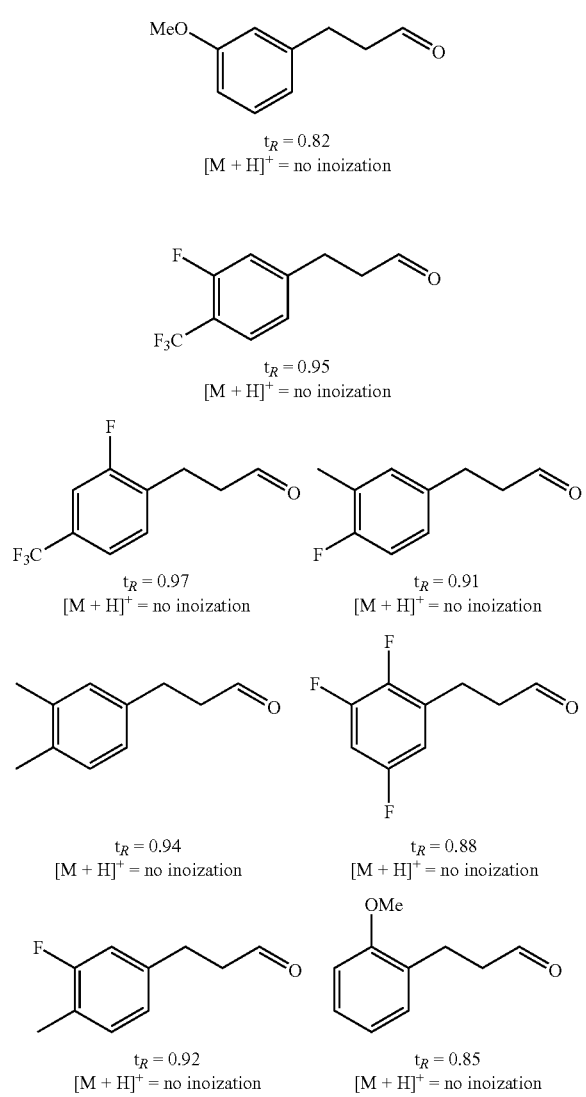

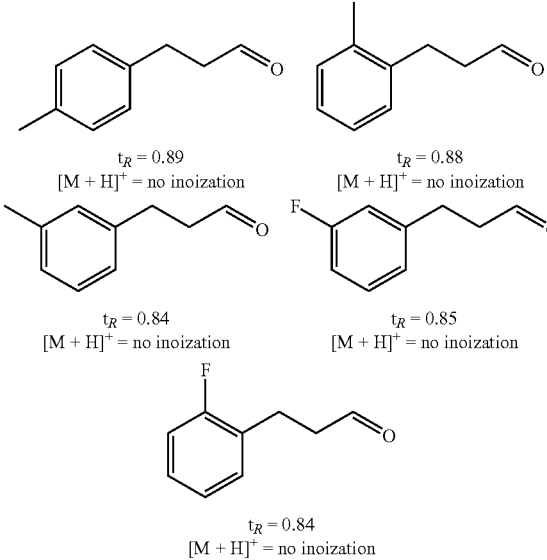

In an inert atmosphere, 3-(trifluoromethyl)benzaldehyde (13.26 g, 76.15 mmol) was dissolved in pyridine (58 ml) and malonic acid (15 g, 145 mmol) was added and the mixture was warmed to 50° C. followed by slow addition (over 5 minutes) of piperidine (5.8 ml, 58.6 mmol). The resulting suspension was warmed to 75° C. and stirring was continued for 3.5 h. The reaction mixture was cooled to 0° C. and poured onto an ice-cold solution of concentrated hydrochloric acid (12 M, 32 ml) in water (400 ml). The precipitated product was filtered off and dried at HV to give 14.21 g (68%) of 3-(3-trifluoromethyl-phenyl)-acrylic acid. LC-MS: $t_R$=0.88 min; $[M+H]^+$=no ionisation.

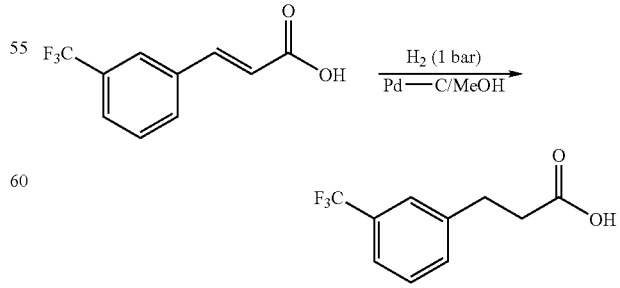

In an inert atmosphere, Pd—C (10%, 2.84 g) was suspended in methanol (130 ml) followed by the addition of a solution of 3-(3-trifluoromethyl-phenyl)-acrylic acid (14.21 g, 65.7 mmol). The reaction mixture was put under an atmosphere of hydrogen (1 bar) and vigorously stirred for 2.5 h. The reaction mixture was filtered over a pad of celite and concentrated under reduced pressure to give 12.39 g (86%) of 3-(3-trifluoromethyl-phenyl)-propionic acid. LC-MS: $t_R$=0.87 min; [M+H]$^+$=no ionisation.

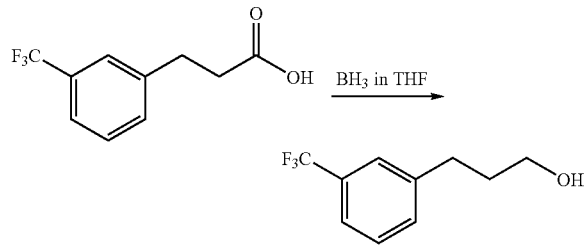

3-(3-Trifluoromethyl-phenyl)-propionic acid (12.4 g, 57 mmol) was dissolved in THF (160 ml) in an inert atmosphere and cooled to 0° C. followed by slow addition of borane in THF (85 ml, 85 mmol). Stirring was continued at 0° C. for 1 h and at rt for 24 h. The mixture was cooled to 0° C. and methanol (100 ml) and water (100 ml) was carefully added. The organic solvents were removed under reduced pressure. The remaining aqueous layer was extracted with DCM (3×100 ml). The combined organic layers were washed with brine, dried over magnesium sulfate, filtered and concentrated under reduced pressure. The crude product was purified by flash chromatography (silicagel, DCM/methanol=9/1) to give 10.97 g (94%) of 3-(3-trifluoromethyl-phenyl)-propan-1-ol. LC-MS: $t_R$=0.87 min; [M+H]$^+$=no ionisation.

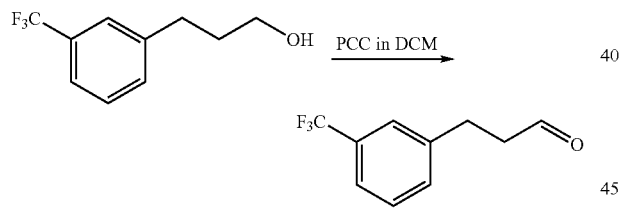

According to the procedure described above for the preparation of 3-(4-trifluoromethyl-phenyl)-propionaldehyde by PCC-oxidation, 132 mg (44%) of 3-(3-trifluoromethyl-phenyl)-propionaldehyde {LC-MS: $t_R$=0.89 min; [M+H]$^+$=no ionization} was obtained from 3-(3-trifluoromethyl-phenyl)-propan-1-ol (300 mg, 1.5 mmol).

According to the procedure described for the preparation of 3-(3-trifluoromethyl-phenyl)-propionaldehyde, the following substituted 3-phenyl-propionaldehyde derivatives were prepared:

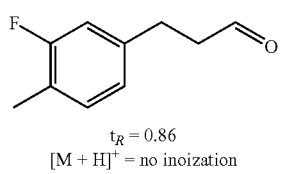

$t_R$ = 0.86
[M + H]$^+$ = no inoization

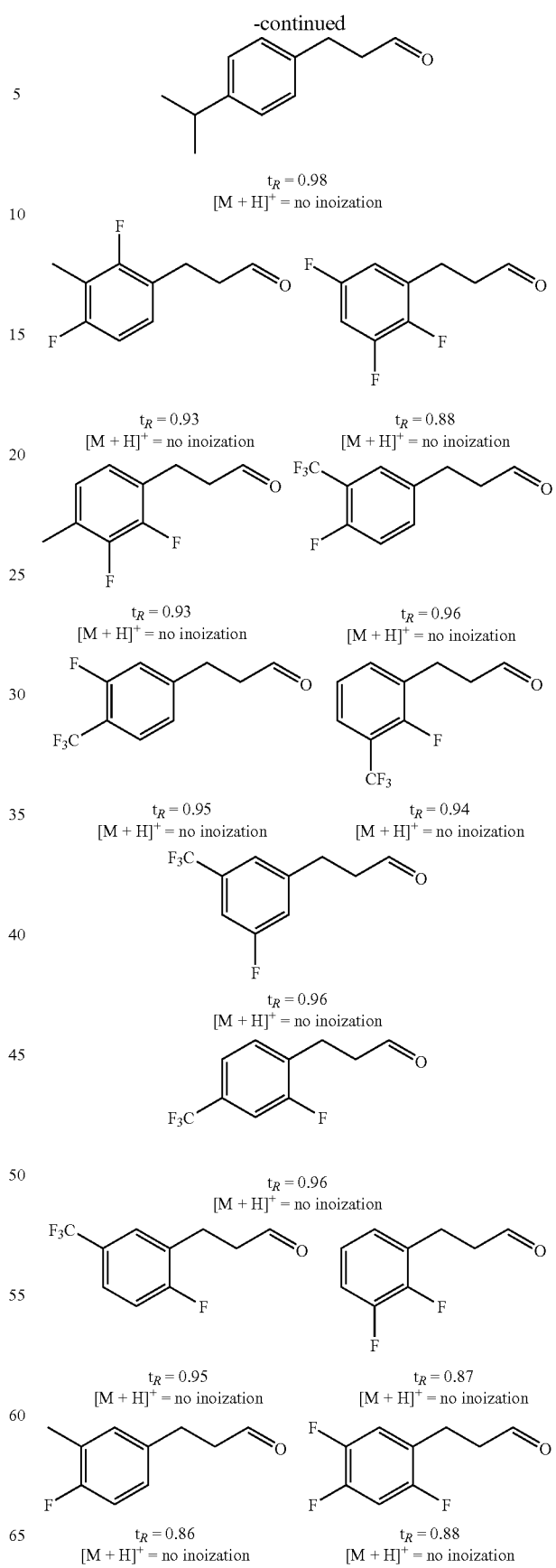

-continued

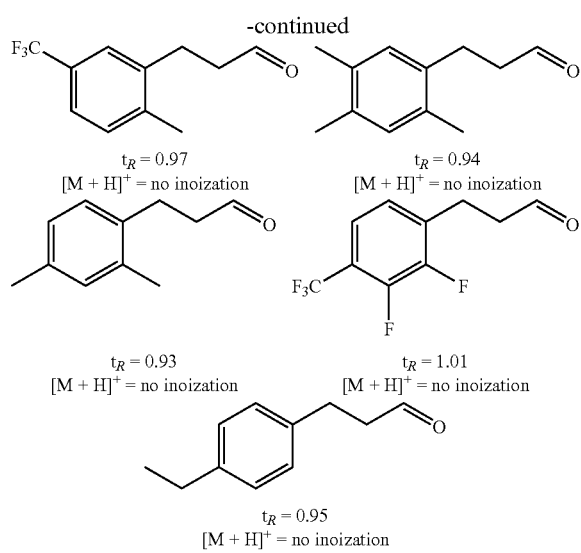

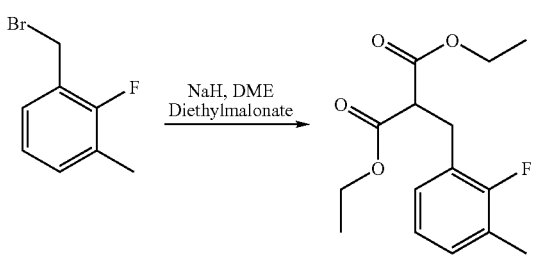

To a suspension of sodium hydride (215 mg, 4.92 mmol) in dimethoxyethane (3 ml) was added dropwise a solution of diethyl malonate (868 mg, 5.42 mmol) in dimethoxyethane (2 ml) in an inert atmosphere at rt. Stirring was continued for 1 h followed by the addition of a solution of 2-fluoro-3-methyl-benzylbromide (1 g, 4.92 mmol) in dimethoxyethane (15 ml). The reaction mixture was refluxed for 90 minutes, cooled again to rt and water (5 ml) was carefully added. The diemthoxyethane was removed under reduced pressure, DCM (100 ml) was added and the organic layer was washed with water (100 ml), dried over magenisum sulfate, filtered and concentrated under reduced pressure. The crude product was purified by flash chromatography (silicagel, DCM/heptane=4/1) to give 973 mg (70%) of 2-(2-fluoro-3-methyl-benzyl)-malonic acid diethyl ester. LC-MS: $t_R$=1.03 min; [M+H]$^+$=283.22.

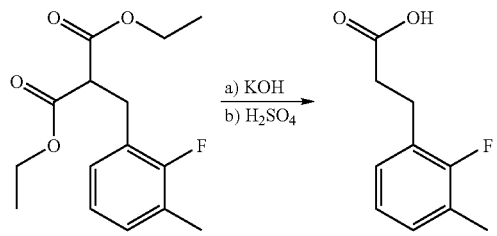

Potassium hydroxide (387 mg, 6.9 mmol) was dissolved in water (8 ml) followed by the addition of 2-(2-fluoro-3-methyl-benzyl)-malonic acid diethyl ester (973 mg, 3.44 mmol). The mixture was refluxed for 5 h followed by removal of the ethanol under reduced pressure. Concentrated sulfuric acid (0.59 ml) was added to the remaining aqueous solution and refluxing was continued for 18 h. The reaction mixture was cooled to 0° C. and the precipitated product was filtered off, washed with water and dried at HV to give 433 mg (69%) of 3-(2-fluoro-3-methyl-phenyl)-propionic acid. LC-MS: $t_R$=0.84 min; [M+H]$^+$=183.20.

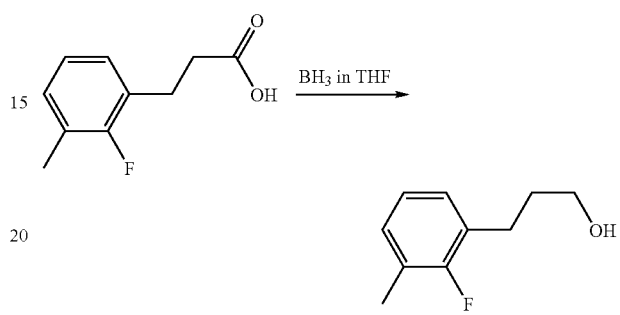

According to procedures described above, 3-(2-fluoro-3-methyl-phenyl)-propionic acid (2.39 g, 13.12 mmol) was reduced by borane in THF to give 1.82 g (82.5%) of 3-(2-fluoro-3-methyl-phenyl)-propan-1-ol. LC-MS: $t_R$=0.86 min; [M+H]$^+$=no ionization.

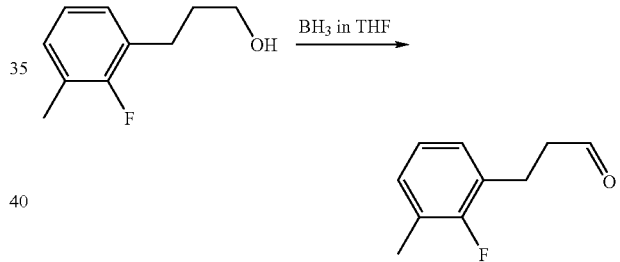

According to procedures described above, 3-(2-fluoro-3-methyl-phenyl)-propan-1-ol (300 mg, 1.78 mmol) was oxidized by PCC in DCM to give 178 mg (60%) of 3-(2-fluoro-3-methyl-phenyl)-propionaldehyde. LC-MS: $t_R$=0.86 min; [M+H]$^+$=no ionization.

According to the procedure described for the preparation of 3-(2-fluoro-3-methyl-phenyl)-propionaldehyde, the following substituted 3-phenyl-propionaldehyde derivatives were prepared:

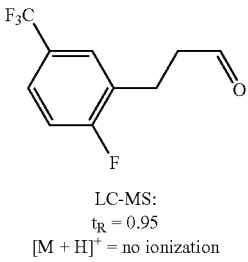

LC-MS:
$t_R$ = 0.95
[M + H]$^+$ = no ionization

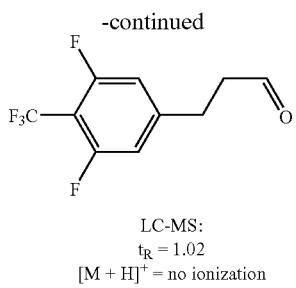

LC-MS:
$t_R = 1.02$
$[M + H]^+$ = no ionization

Preparation of Final Compounds

Example 1

2-{1-Ethyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide

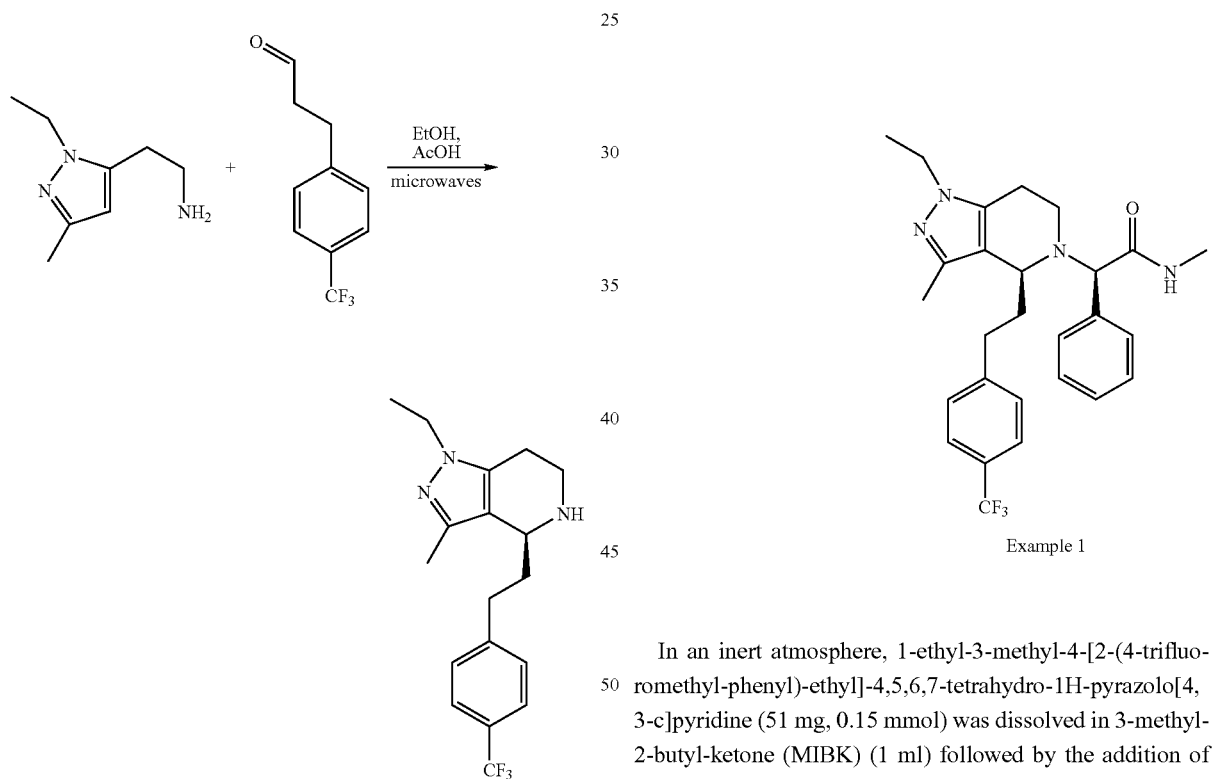

Example 1

2-(2-Ethyl-5-methyl-2H-pyrazol-3-yl)-ethylamine (148 mg, 0.97 mmol) was dissolved in ethanol (3 ml) and acetic acid (116.5 mg. 1.94 mmol) was added followed by the addition of 3-(4-trifluoromethyl-phenyl)-propionaldehyde (197 mg, 0.97 mmol). The mixture was sealed and put in the microwave oven (100 Watts; 130° C., 14 bar, 6 minutes). The solvents were removed under reduced pressure and the residue was purified by prep. HPLC to give 113 mg (34.5%) of 1-ethyl-3-methyl-4-[2-(4-trifluoromethyl-phenyl)-ethyl]-4,5,6,7-tetrahydro-1H-pyrazolo[4,3-c]pyridine. LC-MS: $t_R$=0.75 min; $[M+H]^+$=338.22.

In an inert atmosphere, 1-ethyl-3-methyl-4-[2-(4-trifluoromethyl-phenyl)-ethyl]-4,5,6,7-tetrahydro-1H-pyrazolo[4,3-c]pyridine (51 mg, 0.15 mmol) was dissolved in 3-methyl-2-butyl-ketone (MIBK) (1 ml) followed by the addition of DIPEA (21.3 mg, 0.165 mmol) and toluene-4-sulfonic acid methylcarbamoyl-phenyl-methyl ester (71.8 mg, 0.225 mmol). The reaction mixture was heated to 90° C. for 24 h, concentrated in vacuo and the crude product was purified by prep. HPLC to give 70 mg (95%) of 2-{1-ethyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide. LC-MS: $t_R$=0.84 min; $[M+H]^+$=485.28.

According to the procedure described for the preparation of example 1 the following examples 2 to 9 could be prepared:

Example 2

2-{1-Ethyl-4-[2-(4-ethyl-phenyl)-ethyl]-3-methyl-1,4,6,7-tetrahydro-pyrazolo[4,3-c]pyridin-5-yl}-N-methyl-2-phenyl-acetamide

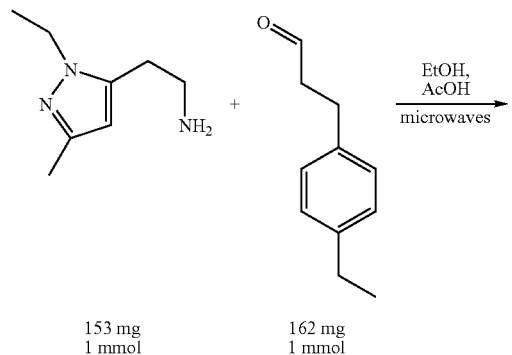

153 mg
1 mmol 162 mg
1 mmol 22.5 mg yield
0.076 mmol
$t_R$ = 0.75 min
$[M + H]^+$ = 298.21

79.5 mg
0.25 mmol

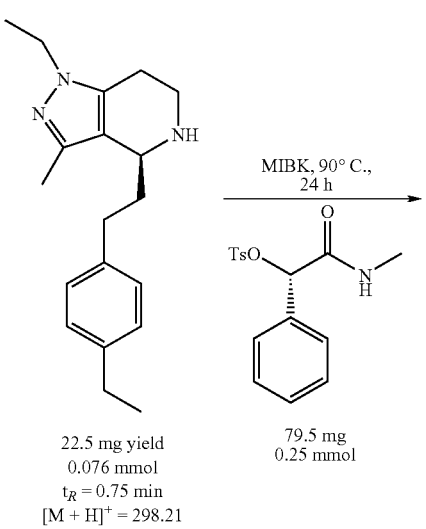

Example 2
2 mg yield
0.0045 mmol
$t_R$ = 0.85 min
$[M + H]^+$ = 445.26

Example 3

2-{1-Ethyl-4-[2-(2-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide

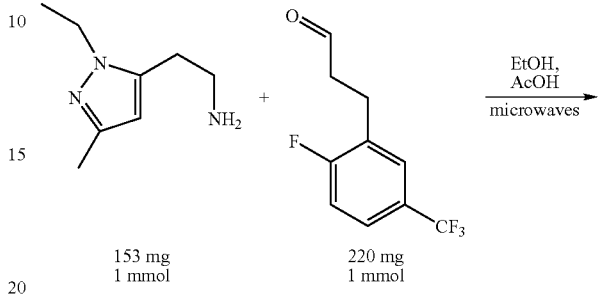

153 mg
1 mmol 220 mg
1 mmol 88.4 mg yield
0.25 mmol
$t_R$ = 0.76 min
$[M + H]^+$ = 356.22

79.5 mg
0.25 mmol

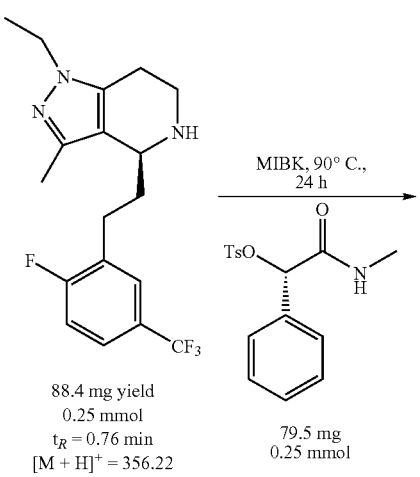

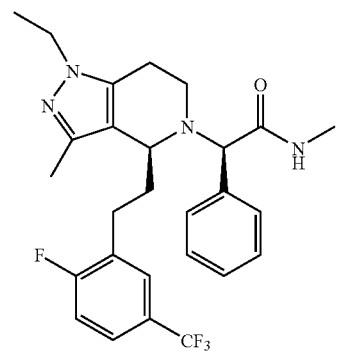

Example 3
27 mg yield
0.053 mmol
$t_R$ = 0.85 min
$[M + H]^+$ = 503.22

Example 4

2-{4-[2-(2,3-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide

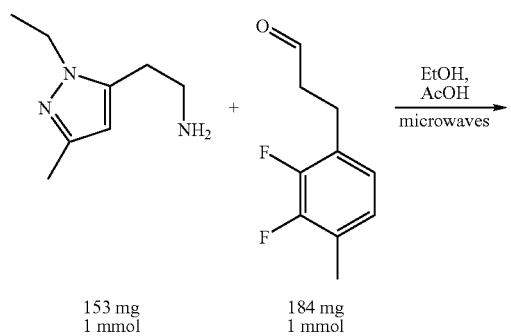

153 mg
1 mmol 184 mg
1 mmol

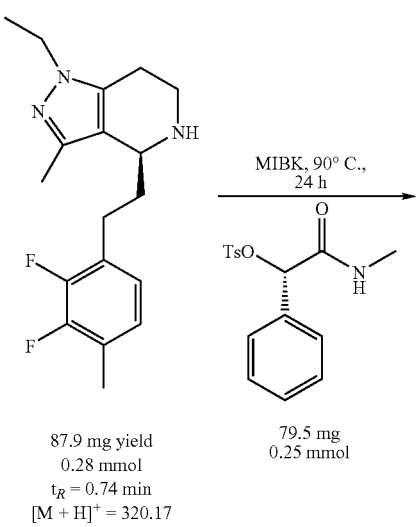

87.9 mg yield
0.28 mmol
$t_R$ = 0.74 min
[M + H]$^+$ = 320.17

79.5 mg
0.25 mmol

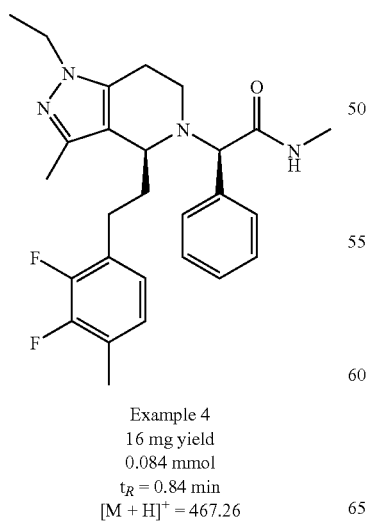

Example 4
16 mg yield
0.084 mmol
$t_R$ = 0.84 min
[M + H]$^+$ = 467.26

Example 5

2-{1-Ethyl-3-methyl-4-[2-(2,3,5-trifluoro-phenyl)-ethyl]-1,4,6,7-tetrahydro-pyrazolo[4,3-c]pyridin-5-yl}-N-methyl-2-phenyl-acetamide

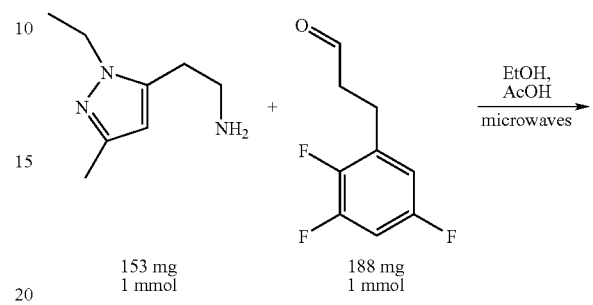

153 mg
1 mmol 188 mg
1 mmol

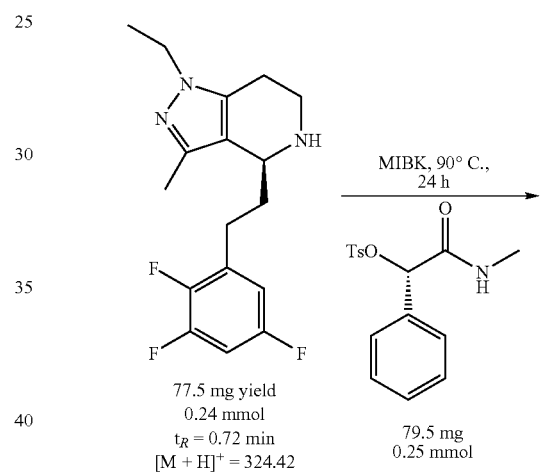

77.5 mg yield
0.24 mmol
$t_R$ = 0.72 min
[M + H]$^+$ = 324.42

79.5 mg
0.25 mmol

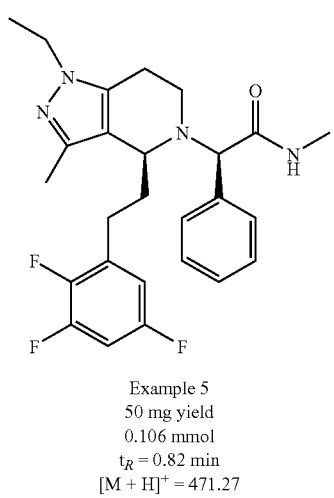

Example 5
50 mg yield
0.106 mmol
$t_R$ = 0.82 min
[M + H]$^+$ = 471.27

Example 6

2-[1-Ethyl-3-methyl-4-(2-p-tolyl-ethyl)-1,4,6,7-tetrahydro-pyrazolo[4,3-c]pyridin-5-yl]-N-methyl-2-phenyl-acetamide

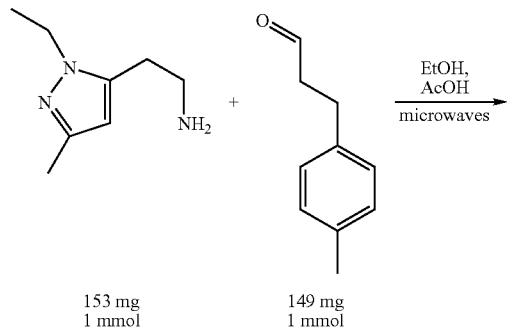

153 mg
1 mmol 149 mg
1 mmol

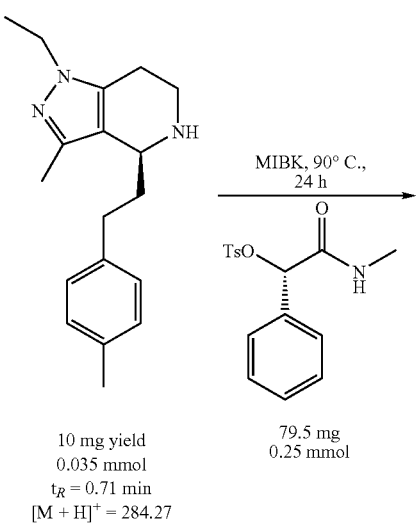

10 mg yield
0.035 mmol
$t_R$ = 0.71 min
$[M + H]^+$ = 284.27

79.5 mg
0.25 mmol

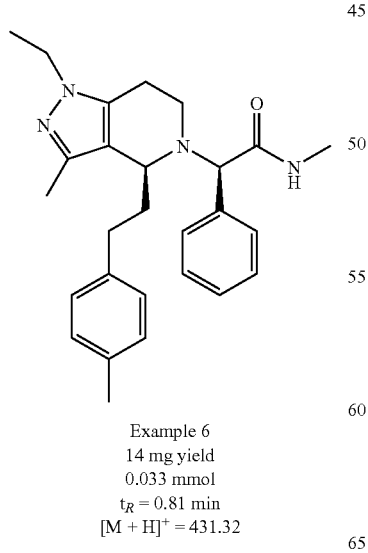

Example 6
14 mg yield
0.033 mmol
$t_R$ = 0.81 min
$[M + H]^+$ = 431.32

Example 7

2-{1-Ethyl-4-[2-(4-fluoro-3-methyl-phenyl)-ethyl]-3-methyl-1,4,6,7-tetrahydro-pyrazolo[4,3-c]pyridin-5-yl}-N-methyl-2-phenyl-acetamide

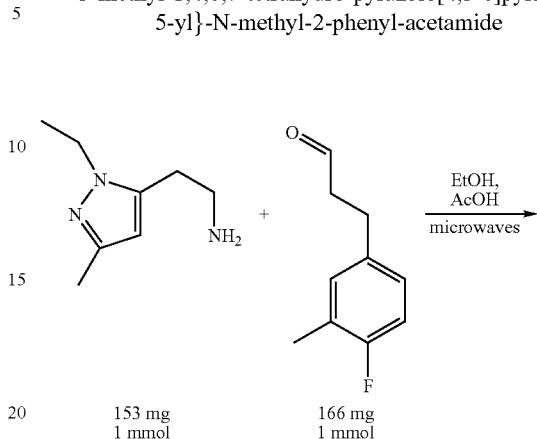

153 mg
1 mmol 166 mg
1 mmol

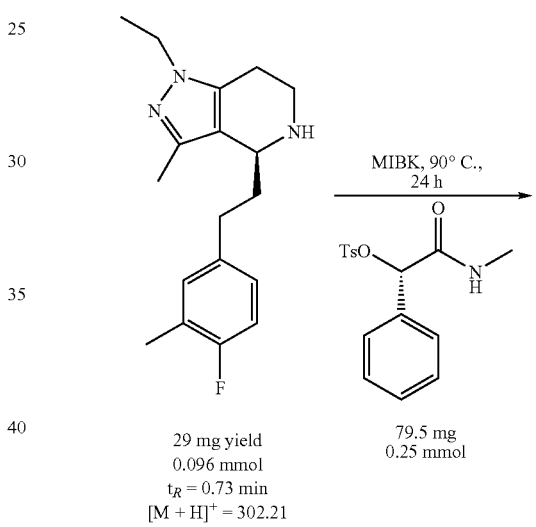

29 mg yield
0.096 mmol
$t_R$ = 0.73 min
$[M + H]^+$ = 302.21

79.5 mg
0.25 mmol

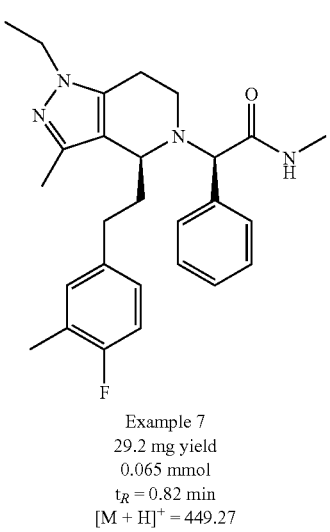

Example 7
29.2 mg yield
0.065 mmol
$t_R$ = 0.82 min
$[M + H]^+$ = 449.27

Example 8

2-{1-Ethyl-3-methyl-4-[2-(3-trifluoromethyl-phenyl)-ethyl]-1,4,6,7-tetrahydro-pyrazolo[4,3-c]pyridin-5-yl}-N-methyl-2-phenyl-acetamide

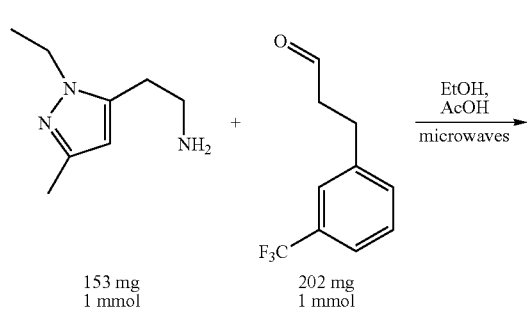

153 mg
1 mmol 202 mg
1 mmol

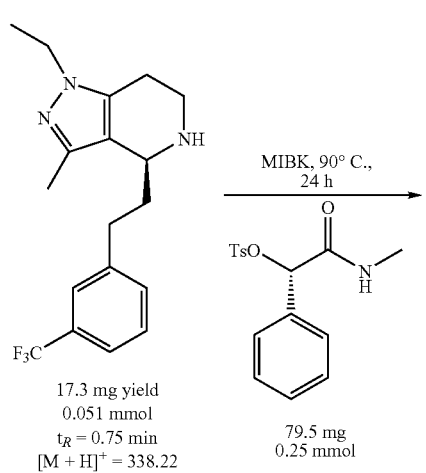

17.3 mg yield
0.051 mmol
$t_R$ = 0.75 min
[M + H]$^+$ = 338.22

79.5 mg
0.25 mmol

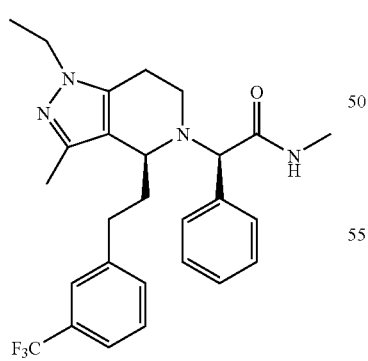

Example 8
16.2 mg yield
0.033 mmol
$t_R$ = 0.84 min
[M + H]$^+$ = 485.28

Example 9

2-[4-(2-Benzo[1,3]dioxol-5-yl-ethyl)-1-ethyl-3-methyl-1,4,6,7-tetrahydro-pyrazolo[4,3-c]pyridin-5-yl]-N-methyl-2-phenyl-acetamide

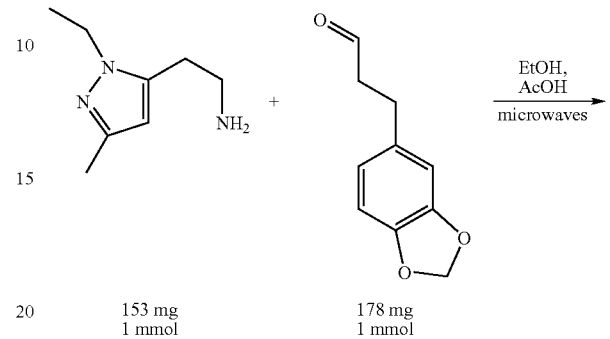

153 mg
1 mmol 178 mg
1 mmol

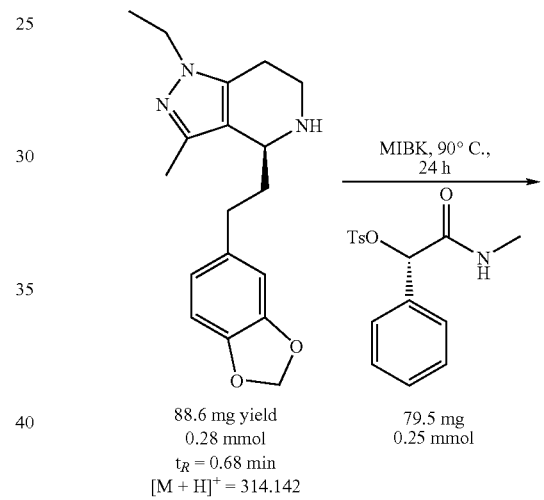

88.6 mg yield
0.28 mmol
$t_R$ = 0.68 min
[M + H]$^+$ = 314.142

79.5 mg
0.25 mmol

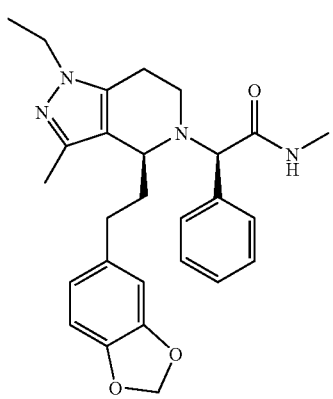

Example 9
40 mg yield
0.086 mmol
$t_R$ = 0.78 min
[M + H]$^+$ = 461.24

According to the sequences described above, the following examples were prepared:

Example 10

2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide

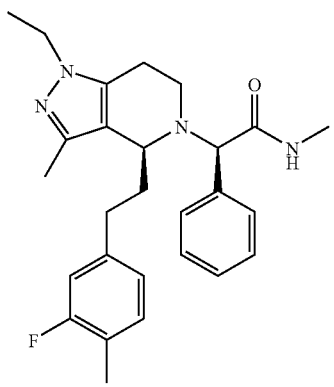

Example 10
29.6 mg yield
$t_R$ = 0.83 min
$[M + H]^+$ = 449.27

Example 11

2-{1-Ethyl-4-[2-(4-isopropyl-phenyl)-ethyl]-3-methyl-1,4,6,7-tetrahydro-pyrazolo[4,3-c]pyridin-5-yl}-N-methyl-2-phenyl-acetamide

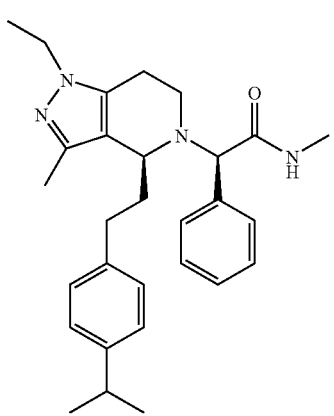

Example 11
39.9 mg yield
$t_R$ = 0.86 min
$[M + H]^+$ = 459.29

Example 12

2-{1-Ethyl-4-[2-(3-fluoro-phenyl)-ethyl]-3-methyl-1,4,6,7-tetrahydro-pyrazolo[4,3-c]pyridin-5-yl}-N-methyl-2-phenyl-acetamide

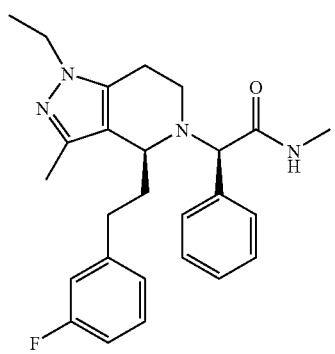

Example 12
38.4 mg yield
$t_R$ = 0.82 min
$[M + H]^+$ = 435.36

Example 13

2-{1-Ethyl-4-[2-(2-fluoro-4-methyl-phenyl)-ethyl]-3-methyl-1,4,6,7-tetrahydro-pyrazolo[4,3-c]pyridin-5-yl}-N-methyl-2-phenyl-acetamide

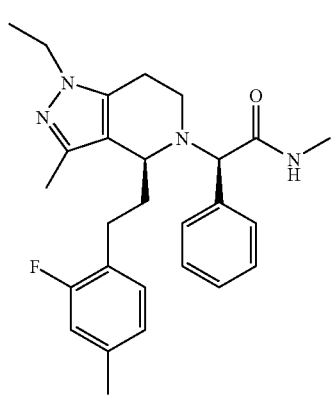

Example 13
20.4 mg yield
$t_R$ = 0.83 min
$[M + H]^+$ = 449.25

Example 14

2-{4-[2-(2,3-Difluoro-phenyl)-ethyl]-1-ethyl-3-methyl-1,4,6,7-tetrahydro-pyrazolo[4,3-c]pyridin-5-yl}-N-methyl-2-phenyl-acetamide

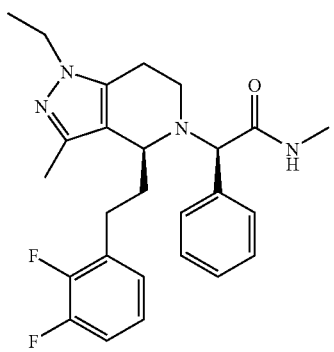

Example 14
63.1 mg yield
$t_R$ = 0.81 min
$[M + H]^+$ = 453.25

Example 15

2-{1-Ethyl-4-[2-(2-fluoro-3-methyl-phenyl)-ethyl]-3-methyl-1,4,6,7-tetrahydro-pyrazolo[4,3-c]pyridin-5-yl}-N-methyl-2-phenyl-acetamide

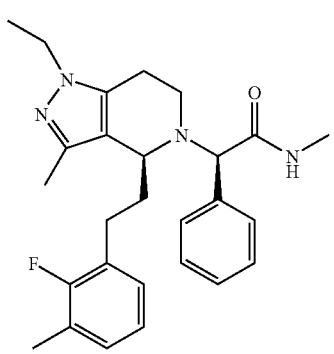

Example 15
68.3 mg yield
$t_R$ = 0.83 min
$[M + H]^+$ = 449.27

Example 16

2-{4-[2-(4-Chloro-phenyl)-ethyl]-1-ethyl-3-methyl-1,4,6,7-tetrahydro-pyrazolo[4,3-c]pyridin-5-yl}-N-methyl-2-phenyl-acetamide

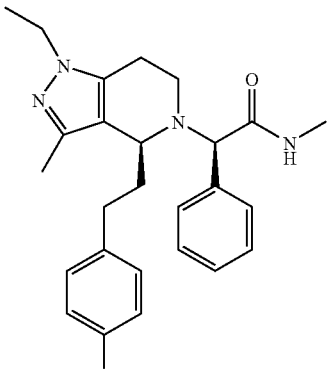

Example 16
13.9 mg yield
$t_R$ = 0.82 min
$[M + H]^+$ = 451.25

Example 17

2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide

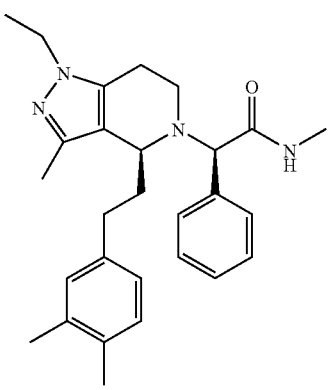

Example 17
51.1 mg yield
$t_R$ = 0.83 min
$[M + H]^+$ = 445.29

Example 18

2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide

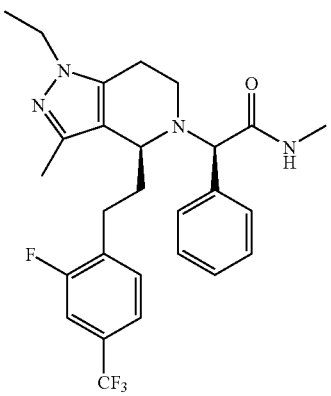

Example 18
62.7 mg yield
$t_R$ = 0.84 min
$[M + H]^+$ = 503.27

Example 19

2-{1,3-Dimethyl-4-[2-(4-trifluoromethyl-phenyl)-ethyl]-1,4,6,7-tetrahydro-pyrazolo[4,3-c]pyridin-5-yl}-N-methyl-2-phenyl-acetamide

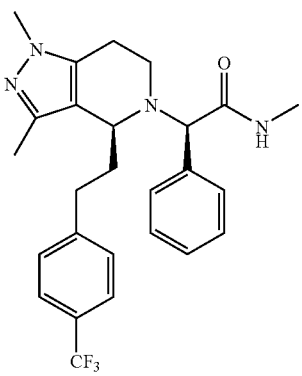

Example 19
123 mg yield
$t_R$ = 0.83 min
$[M + H]^+$ = 471.40

Example 20

2-{1-Ethyl-3-methyl-4-[2-(4-methyl-3-trifluoromethyl-phenyl)-ethyl]-1,4,6,7-tetrahydro-pyrazolo[4,3-c]pyridin-5-yl}-N-methyl-2-phenyl-acetamide

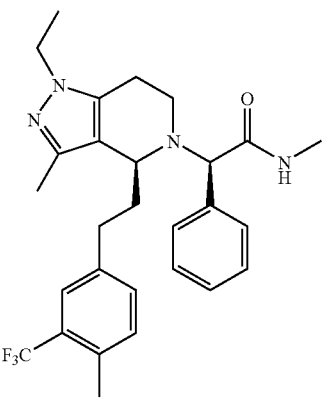

Example 20

69 mg yield
$t_R$ = 0.86 min
$[M + H]^+$ = 499.24

Example 21

2-[1-Ethyl-3-methyl-4-(2-m-tolyl-ethyl)-1,4,6,7-tetrahydro-pyrazolo[4,3-c]pyridin-5-yl]-N-methyl-2-phenyl-acetamide

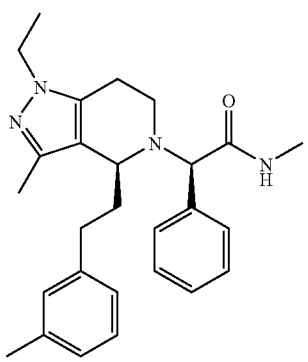

Example 21

11.6 mg yield
$t_R$ = 0.81 min
$[M + H]^+$ = 431.31

Example 22

2-[1-Ethyl-3-methyl-4-(2-o-tolyl-ethyl)-1,4,6,7-tetrahydro-pyrazolo[4,3-c]pyridin-5-yl]-N-methyl-2-phenyl-acetamide

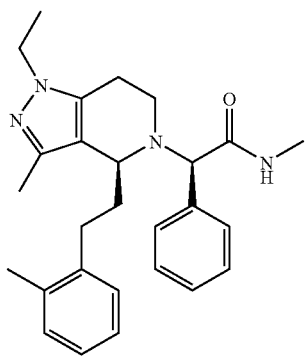

Example 22

40.4 mg yield
$t_R$ = 0.82 min
$[M + H]^+$ = 431.42

Example 23

2-{1-Butyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide

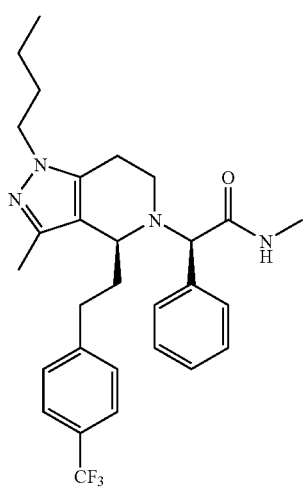

Example 23

40.4 mg yield
$t_R$ = 0.91 min
$[M + H]^+$ = 513.53

Example 24

2-{1-Ethyl-4-[2-(2-fluoro-phenyl)-ethyl]-3-methyl-1,4,6,7-tetrahydro-pyrazolo[4,3-c]pyridin-5-yl}-N-methyl-2-phenyl-acetamide

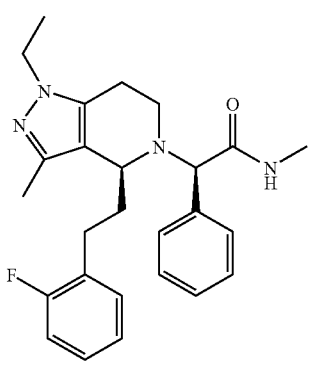

Example 24

17.4 mg yield
$t_R$ = 0.81 min
$[M + H]^+$ = 435.23

Example 25

2-{1-Ethyl-4-[2-(3-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide

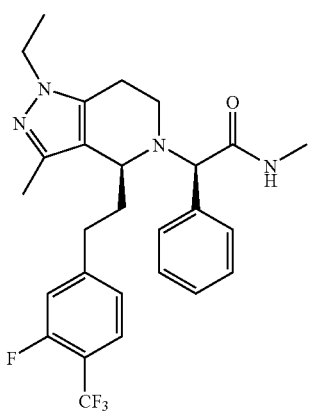

Example 25

72.3 mg yield
$t_R$ = 0.83 min
$[M + H]^+$ = 503.25

Example 26

2-{1-Ethyl-4-[2-(2-fluoro-3-trifluoromethyl-phenyl)-ethyl]-3-methyl-1,4,6,7-tetrahydro-pyrazolo[4,3-c]pyridin-5-yl}-N-methyl-2-phenyl-acetamide

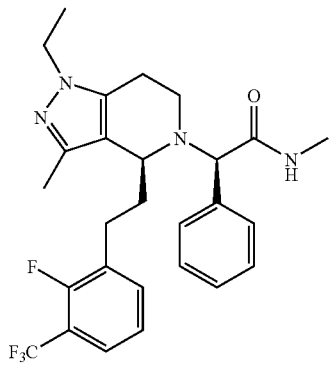

Example 26

11.8 mg yield
$t_R$ = 0.86 min
$[M + H]^+$ = 503.2

Example 27

2-{1-Benzyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide

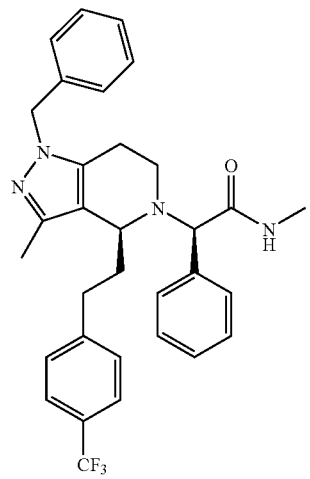

Example 27

11.4 mg yield
$t_R$ = 0.93 min
$[M + H]^+$ = 547.48

Example 28

2-{1-Ethyl-4-[2-(2-methoxy-phenyl)-ethyl]-3-methyl-1,4,6,7-tetrahydro-pyrazolo[4,3-c]pyridin-5-yl}-N-methyl-2-phenyl-acetamide

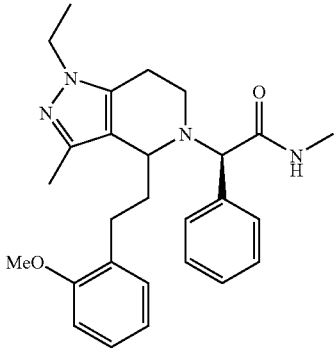

Example 28

38.5 mg yield
$t_R$ = 0.80 min
$[M + H]^+$ = 447.32

Example 29

N-Methyl-2-{3-methyl-1-phenethyl-4-[2-(4-trifluoromethyl-phenyl)-ethyl]-1,4,6,7-tetrahydro-pyrazolo[4,3-c]pyridin-5-yl}-2-phenyl-acetamide

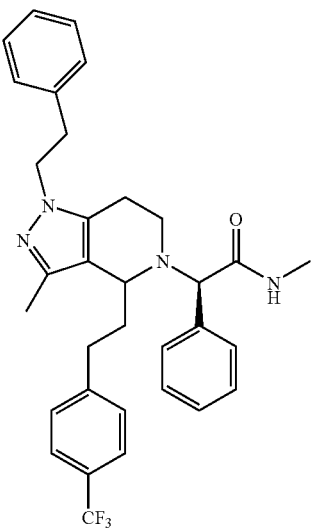

Example 29

20.8 mg yield
$t_R$ = 0.94 min
$[M + H]^+$ = 561.49

Example 30

N-Methyl-2-{3-methyl-1-(2,2,2-trifluoro-ethyl)-4-[2-(4-trifluoromethyl-phenyl)-ethyl]-1,4,6,7-tetrahydro-pyrazolo[4,3-c]pyridin-5-yl}-2-phenyl-acetamide

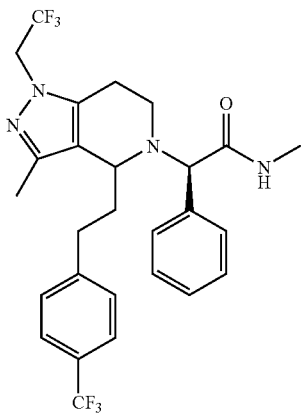

Example 30

7 mg yield
$t_R$ = 0.92 min
$[M + H]^+$ = 539.41

Example 31

2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide

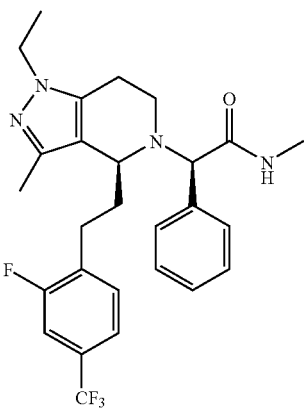

Example 31

42 mg yield
$t_R$ = 0.87 min
$[M + H]^+$ = 503.39

Example 32

2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide

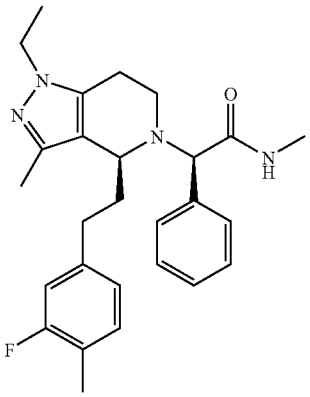

Example 32

33 mg yield
$t_R$ = 0.83 min
$[M + H]^+$ = 449.41

Example 33

2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide

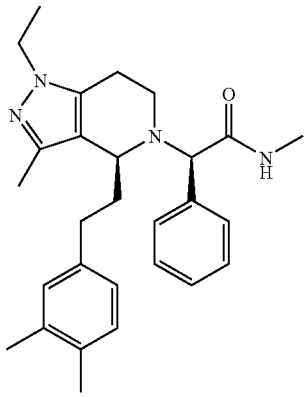

Example 33

28 mg yield
$t_R$ = 0.84 min
$[M + H]^+$ = 445.44

Example 34

2-{1-Ethyl-4-[2-(2-fluoro-3-methyl-phenyl)-ethyl]-3-methyl-1,4,6,7-tetrahydro-pyrazolo[4,3-c]pyridin-5-yl}-N-methyl-2-phenyl-acetamide

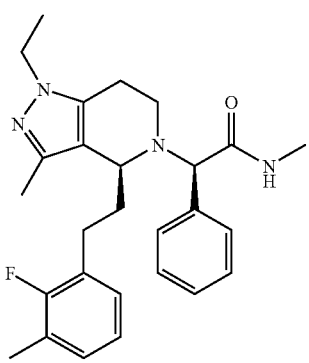

26 mg yield
$t_R$ = 0.83 min
$[M + H]^+$ = 449.43

Example 35

2-{4-[2-(2,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide

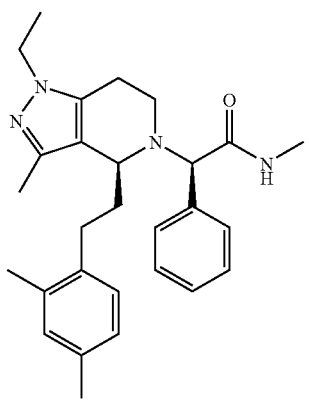

Example 35
124 mg yield
$t_R$ = 0.84 min
$[M + H]^+$ = 445.47

Example 36

2-{4-[2-(2,4-Difluoro-3-methyl-phenyl)-ethyl]-1-ethyl-3-methyl-1,4,6,7-tetrahydro-pyrazolo[4,3-c]pyridin-5-yl}-N-methyl-2-phenyl-acetamide

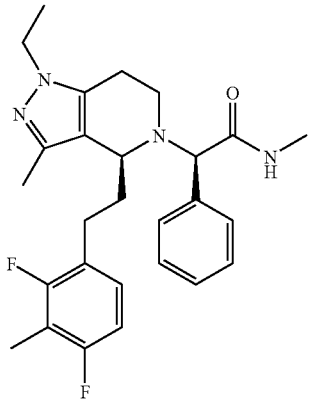

Example 36
41 mg yield
$t_R$ = 0.85 min
$[M + H]^+$ = 467.44

Example 37

2-{1-Ethyl-3-methyl-4-[2-(2,4,5-trifluoro-phenyl)-ethyl]-1,4,6,7-tetrahydro-pyrazolo[4,3-c]pyridin-5-yl}-N-methyl-2-phenyl-acetamide

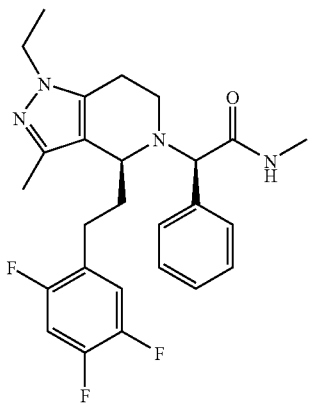

Example 37
76 mg yield
$t_R$ = 0.83 min
$[M + H]^+$ = 471.43

Example 38

2-{1-Ethyl-3-methyl-4-[2-(2,3,4-trifluoro-phenyl)-ethyl]-1,4,6,7-tetrahydro-pyrazolo[4,3-c]pyridin-5-yl}-N-methyl-2-phenyl-acetamide

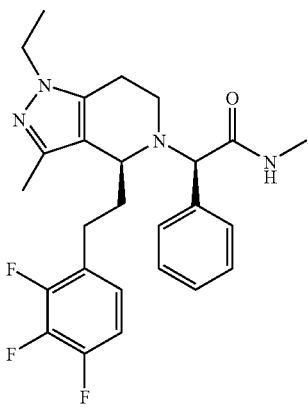

Example 38
51 mg yield
$t_R = 0.83$ min
$[M + H]^+ = 471.43$

Example 39

2-{1-Ethyl-3-methyl-4-[2-(2,3,4-trifluoro-phenyl)-ethyl]-1,4,6,7-tetrahydro-pyrazolo[4,3-c]pyridin-5-yl}-N-methyl-2-phenyl-acetamide

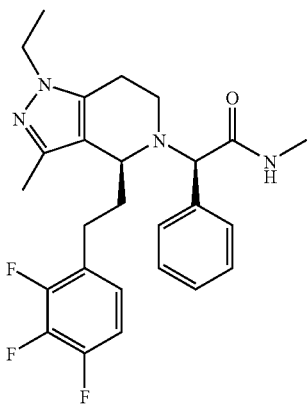

Example 39
24 mg yield
$t_R = 0.86$ min
$[M + H]^+ = 503.38$

Example 40

2-{1-Ethyl-3-methyl-4-[2-(2-methyl-5-trifluoromethyl-phenyl)-ethyl]-1,4,6,7-tetrahydro-pyrazolo[4,3-c]pyridin-5-yl}-N-methyl-2-phenyl-acetamide

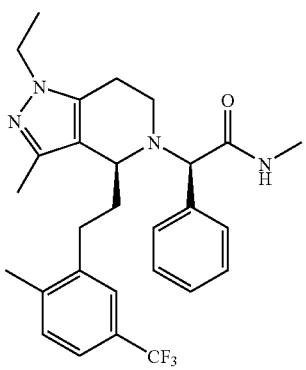

Example 40
70 mg yield
$t_R = 0.80$ min
$[M + H]^+ = 499.43$

Example 41

2-{1-Ethyl-4-[2-(3-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide

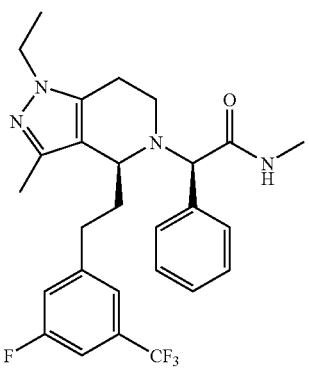

Example 41
83 mg yield
$t_R = 0.87$ min
$[M + H]^+ = 503.41$

Example 42

2-{4-[2-(3,5-Bis-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide

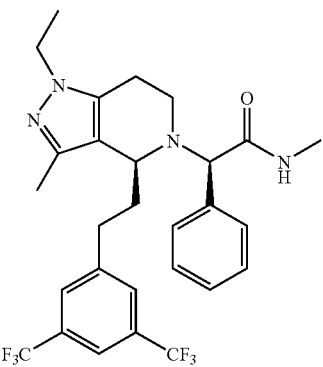

Example 42
75 mg yield
$t_R$ = 0.91 min
$[M + H]^+$ = 553.38

Example 43

2-{4-[2-(3,5-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide

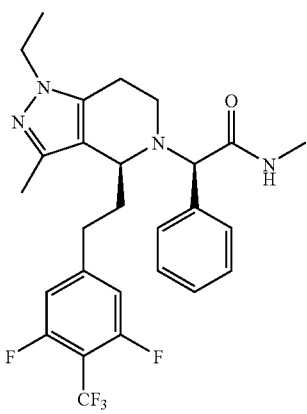

Example 43
99 mg yield
$t_R$ = 0.90 min
$[M + H]^+$ = 521.24

Example 44

2-{4-[2-(3,5-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide

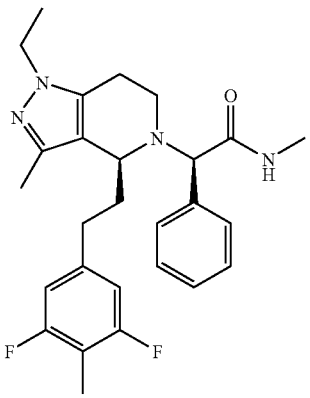

Example 44
71.7 mg yield
$t_R$ = 0.86 min
$[M + H]^+$ = 467.29

Example 45

2-{4-[2-(2,3-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide

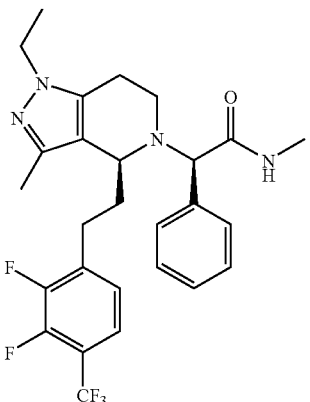

Example 45
125 mg yield
$t_R$ = 0.89 min
$[M + H]^+$ = 521.53

Example 46

2-{4-[2-(3,4-Dichloro-phenyl)-ethyl]-1-ethyl-3-methyl-1,4,6,7-tetrahydro-pyrazolo[4,3-c]pyridin-5-yl}-N-methyl-2-phenyl-acetamide Example 46
800 mg yield
$t_R = 0.86$ min
$[M + H]^+ = 485.52$

Example 47

2-{4-[2-(2,6-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide Example 47
10 mg yield
$t_R = 0.91$ min
$[M + H]^+ = 521.23$

Biological Assays

In Vitro Assay

The orexin receptor antagonistic activity of the compounds of formula (I) and/or (Ia) is determined in accordance with the following experimental method.

Experimental Method:

Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% inactivated fetal calf serum (FCS). The cells are seeded at 80'000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in methanol:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 µl HBSS containing 2.5 mM probenecid, 0.1% BSA, 2 mM HEPES. 100 µl of that same buffer is left in each well.

Within the Fluorescent Imaging Plate Reader (FLIPR, Molecular Devices), antagonists are added to the plate in a volume of 50 µl, incubated for 20 min and finally 100 µl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. Antagonistic activities of compounds are in the nanomolar range with respect to $OX_1$ and $OX_2$ receptors. Selected compounds are displayed in Table 1.

TABLE 1

| Example No | $IC_{50}$ OX1 in nM | $IC_{50}$ OX2 in nM |
| --- | --- | --- |
| Example 3 | 49 | 3 |
| Example 6 | 75 | 4 |
| Example 31 | 52 | 8 |
| Example 32 | 49 | 2 |
| Example 33 | 20 | 4 |
| Example 35 | 131 | 7 |

The invention claimed is:

1. A compound of the general formula Ia with the chirality as depicted below

General Formula Ia
R-chirality

S-chirality wherein
Y represents —CH$_2$—CH2$_2$-;
R$^1$ represents 1,3-benzodioxole or an optionally substituted phenyl group,
   wherein the phenyl group can be mono-, di-, or tri-substituted, and the substituents are independently selected from the group consisting of (C$_{1-4}$)alkyl, halogen and trifluoromethyl;
R$^2$ represents (C$_{1-4}$)alkyl;
R$^3$ represents (C$_{1-4}$)alkyl;
R$^4$ represents a phenyl group, wherein the phenyl group is unsubstituted or independently mono-, di-, or trisubstituted wherein the substituents are independently selected from the group consisting of (C$_{1-4}$)alkyl and halogen;
R$^5$ represents (C$_{1-4}$)alkyl;
in free base form or pharmaceutically acceptable salt form.

2. A compound according to claim 1, wherein
Y represents —CH$_2$—CH$_2$—;
R$^1$ represents 1,3-benzodioxole or an optionally substituted phenyl group, wherein the phenyl group can be mono-, di-, or tri-substituted, wherein the substituents are independently selected from the group consisting of methyl, ethyl, fluorine, chlorine and trifluoromethyl;
R$^2$ represents methyl;
R$^3$ represents ethyl;
R$^4$ represents a phenyl group;
R$^5$ represents methyl.

3. A compound according to claim 1, wherein
Y represents —CH$_2$—CH$_2$—;
R$^1$ represents 1,3-benzodioxole or an optionally substituted phenyl group, wherein the phenyl group can be mono-, di-, or tri-substituted, wherein the substituents are independently selected from the group consisting of (C$_{1-4}$)alkyl, halogen and trifluoromethyl;
R$^2$ represents (C$_{1-4}$)alkyl;
R$^3$ represents (C$_{1-4}$)alkyl;
R$^4$ represents a phenyl group;
R$^5$ represents (C$_{1-4}$)alkyl.

4. A compound according to claim 1 selected from the group consisting of:
   2-{1-Ethyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide;
   2-{1-Ethyl-4-[2-(4-ethyl-phenyl)-ethyl]-3-methyl-1,4,6,7-tetrahydro-pyrazolo[4,3-c]pyridin-5-yl}-N-methyl-2-phenyl-acetamide;
   2-{1-Ethyl-4-[2-(2-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide;
   2-{4-[2-(2,3-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide;
   2-{1-Ethyl-3-methyl-4-[2-(2,3,5-trifluoro-phenyl)-ethyl]-1,4,6,7-tetrahydro-pyrazolo[4,3-c]pyridin-5-yl}-N-methyl-2-phenyl-acetamide;
   2-[1-Ethyl-3-methyl-4-(2-p-tolyl-ethyl)-1,4,6,7-tetrahydro-pyrazolo[4,3-c]pyridin-5-yl]-N-methyl-2-phenyl-acetamide;
   2-{1-Ethyl-4-[2-(4-fluoro-3-methyl-phenyl)-ethyl]-3-methyl-1,4,6,7-tetrahydro-pyrazolo[4,3-c]pyridin-5-yl}-N-methyl-2-phenyl-acetamide;
   2-{1-Ethyl-3-methyl-4-[2-(3-trifluoromethyl-phenyl)-ethyl]-1,4,6,7-tetrahydro-pyrazolo[4,3-c]pyridin-5-yl}-N-methyl-2-phenyl-acetamide;
   2-[4-(2-Benzo[1,3]dioxol-5-yl-ethyl)-1-ethyl-3-methyl-1,4,6,7-tetrahydro-pyrazolo[4,3-c]pyridin-5-yl]-N-methyl-2-phenyl-acetamide;
   2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide;
   2-{1-Ethyl-4-[2-(4-isopropyl-phenyl)-ethyl]-3-methyl-1,4,6,7-tetrahydro-pyrazolo[4,3-c]pyridin-5-yl}-N-methyl-2-phenyl-acetamide,
   2-{1-Ethyl-4-[2-(3-fluoro-phenyl)-ethyl]-3-methyl-1,4,6,7-tetrahydro-pyrazolo[4,3-c]pyridin-5-yl}-N-methyl-2-phenyl-acetamide;
   2-{1-Ethyl-4-[2-(2-fluoro-4-methyl-phenyl)-ethyl]-3-methyl-1,4,6,7-tetrahydro-pyrazolo[4,3-c]pyridin-5-yl}-N-methyl-2-phenyl-acetamide;
   2-{4-[2-(2,3-Difluoro-phenyl)-ethyl]-1-ethyl-3-methyl-1,4,6,7-tetrahydro-pyrazolo[4,3-c]pyridin-5-yl}-N-methyl-2-phenyl-acetamide;
   2-{1-Ethyl-4-[2-(2-fluoro-3-methyl-phenyl)-ethyl]-3-methyl-1,4,6,7-tetrahydro-pyrazolo[4,3-c]pyridin-5-yl}-N-methyl-2-phenyl-acetamide;
   2-{4-[2-(4-Chloro-phenyl)-ethyl]-1-ethyl-3-methyl-1,4,6,7-tetrahydro-pyrazolo[4,3-c]pyridin-5-yl}-N-methyl-2-phenyl-acetamide;
   2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;
   2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;
   2-{1,3-Dimethyl-4-[2-(4-trifluoromethyl-phenyl)-ethyl]-1,4,6,7-tetrahydro-pyrazolo[4,3-c]pyridin-5-yl}-N-methyl-2-phenyl-acetamide;
   2-{1-Ethyl-3-methyl-4-[2-(4-methyl-3-trifluoromethyl-phenyl)-ethyl]-1,4,6,7-tetrahydro-pyrazolo[4,3-c]pyridin-5-yl}-N-methyl-2-phenyl-acetamide;
   2-[1-Ethyl-3-methyl-4-(2-m-tolyl-ethyl)-1,4,6,7-tetrahydro-pyrazolo[4,3-c]pyridin-5-yl]-N-methyl-2-phenyl-acetamide;
   2-[1-Ethyl-3-methyl-4-(2-o-tolyl-ethyl)-1,4,6,7-tetrahydro-pyrazolo[4,3-c]pyridin-5-yl]-N-methyl-2-phenyl-acetamide;
   2-{1-Butyl-3-methyl-4-[2-(4-trifluoromethyl-phenyl)-ethyl]-1,4,6,7-tetrahydro-pyrazolo[4,3-c]pyridin-5-yl}-N-methyl-2-phenyl-acetamide;
   2-{1-Ethyl-4-[2-(2-fluoro-phenyl)-ethyl]-3-methyl-1,4,6,7-tetrahydro-pyrazolo[4,3-c]pyridin-5-yl}-N-methyl-2-phenyl-acetamide;
   2-{1-Ethyl-4-[2-(3-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;
   2-{1-Ethyl-4-[2-(2-fluoro-3-trifluoromethyl-phenyl)-ethyl]-3-methyl-1,4,6,7-tetrahydro-pyrazolo[4,3-c]pyridin-5-yl}-N-methyl-2-phenyl-acetamide;
   2-{1-Ethyl-4-[2-(2-fluoro-4-trifluoromethyl-phenyl)-ethyl]-1,4,6,7-tetrahydro-pyrazolo[4,3-c]pyridin-5-yl}-N-methyl-2-phenyl-acetamide;
   2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide;

2-{-4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(2-fluoro-3-methyl-phenyl)-ethyl]-3-methyl-1,4,6,7-tetrahydro-pyrazolo[4,3-c]pyridin-5-yl}-N-methyl-2-phenyl-acetamide;

2-{4-[2-(2,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(2,4-Difluoro-3-methyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-3-methyl-4-[2-(2,4,5-trifluoro-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(2,4,5-trifluoro-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(2,3,4-trifluoro-phenyl)-ethyl]-1,4,6,7-tetrahydro-pyrazolo[4,3-c]pyridin-5-yl}-N-methyl-2-phenyl-acetamide;

2-{1-Ethyl-3-methyl-4-[2-(2-methyl-5-trifluoromethyl-phenyl)-ethyl]-1,4,6,7-tetrahydro-pyrazolo[4,3-c]pyridin-5-yl}-N-methyl-2-phenyl-acetamide;

2-{1-Ethyl-4-[2-(3-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide; and 2-{4-[2-(3,5-Bis-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,5-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{-4-[2-(3,5-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide;

2-{-4-[2-(2,3-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,4-Dichloro-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(2,6-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

5. A compound according to claim 1 selected from the group consisting of:

2-{-4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide;

2-{1-Ethyl-4-[2-(2-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide;

2-{4-[2-(2,3-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide; and 2-{1-Ethyl-4-[2-(4-ethyl-phenyl)-ethyl]-3-methyl-1,4,6,7-tetrahydro-pyrazolo[4,3-c]pyridin-5-yl}-N-methyl-2-phenyl-acetamide;

2-{4-[2-(3,5-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide;

2-{4-[2-(3,5-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide.

6. A pharmaceutical composition comprising a compound according to claim 1 and a pharmaceutically acceptable carrier material.

7. A method for the treatment of diseases selected from insomnia or decreased food intake comprising administering to a subject a pharmaceutically active amount of a compound according to claim 1.

8. The compound according to claim 1 wherein said compound is 2-{4-[2-(3,4-Dimethyl-phenyl)-ethyl]-1-ethyl-3-methyl-1,4,6,7-tetrahydro-pyrazolo[4,3-c]pyridin-5-yl}-N-methyl-2-phenyl-acetamide.

9. The compound according to claim 1 wherein said compound is 2-{1-Ethyl-4-[2-(3-fluoro-4-methyl-phenyl)-ethyl]-3-methyl-1,4,6,7-tetrahydro-pyrazolo[4,3-c]pyridin-5-yl}-N-methyl-2-phenyl-acetamide.

10. The compound according to claim 1 wherein said compound is 2-{1-Ethyl-4-[2-(2-fluoro-4-trifluoromethyl-phenyl)-ethyl]-3-methyl-1,4,6,7-tetrahydro-pyrazolo[4,3-c]pyridin-5-yl}-N-methyl-2-phenyl-acetamide.

11. The compound according to claim 1 wherein said compound is 2-{1-Ethyl-4-[2-(2-fluoro-5-trifluoromethyl-phenyl)-ethyl]-3-methyl-1,4,6,7-tetrahydro-pyrazolo[4,3-c]pyridin-5-yl}-N-methyl-2-phenyl-acetamide.

12. The compound according to claim 1 wherein said compound is 2-{-4-[2-(2,3-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide.

13. The compound according to claim 1 wherein said compound is 2-{1-Ethyl-4-[2-(4-ethyl-phenyl)-ethyl]-3-methyl-1,4,6,7-tetrahydro-pyrazolo[4,3-c]pyridin-5-yl}-N-methyl-2-phenyl-acetamide.

14. The compound according to claim 1 wherein said compound is 2-{4-[2-(3,5-Difluoro-4-trifluoromethyl-phenyl)-ethyl]-1-ethyl-3-methyl-1,4,6,7-tetrahydro-pyrazolo[4,3-c]pyridin-5-yl}-N-methyl-2-phenyl-acetamide.

15. The compound according to claim 1 wherein said compound is 2-{4-[2-(3,5-Difluoro-4-methyl-phenyl)-ethyl]-1-ethyl-3-methyl-1,4,6,7-tetrahydro-pyrazolo[4,3-c]pyridin-5-yl}-N-methyl-2-phenyl-acetamide.

16. The pharmaceutical composition according to claim 6, wherein said compound is a compound according to claim 4.

17. The pharmaceutical composition according to claim 6, wherein said compound is a compound according to claim 5.

18. The method according to claim 7, wherein said compound is a compound according to claim 4.

19. The method according to claim 7, wherein said compound is a compound according to claim 5.

* * * * *